US012599286B2

(12) United States Patent
Fridman et al.

(10) Patent No.: US 12,599,286 B2
(45) Date of Patent: Apr. 14, 2026

(54) POWER SOURCES FOR WIRELESS INTRAORAL SCANNERS

(71) Applicant: Align Technology, Inc., San Jose, CA (US)

(72) Inventors: Edi Fridman, Rishon le Zion (IL); Moshe Alboher, Tsoran (IL)

(73) Assignee: Align Technology, Inc., San Jose, CA (US)

( * ) Notice: Subject to any disclaimer, the term of this patent is extended or adjusted under 35 U.S.C. 154(b) by 165 days.

(21) Appl. No.: 18/486,058

(22) Filed: Oct. 12, 2023

(65) Prior Publication Data

US 2024/0122446 A1      Apr. 18, 2024

Related U.S. Application Data

(60) Provisional application No. 63/415,942, filed on Oct. 13, 2022.

(51) Int. Cl.
A61B 1/05 (2006.01)
A61B 1/00 (2006.01)
(Continued)

(52) U.S. Cl.
CPC ...... A61B 1/00036 (2013.01); A61B 1/00006 (2013.01); A61B 1/00016 (2013.01);
(Continued)

(58) Field of Classification Search
CPC ............ A61B 1/00036; A61B 1/00006; A61B 1/00016; A61B 1/00032; A61B 1/00045;
(Continued)

(56) References Cited

U.S. PATENT DOCUMENTS 6,099,314 A      8/2000   Kopelman et al.
6,334,772 B1      1/2002   Taub et al.
(Continued)

OTHER PUBLICATIONS

Reissue U.S. Appl. No. 16/784,493; inventor Babayoff, Noam; filed Feb. 7, 2020.

(Continued)

*Primary Examiner* — Howard D Brown, Jr.
(74) *Attorney, Agent, or Firm* — Lowenstein Sandler LLP

(57)      ABSTRACT

In embodiments set forth herein, an intraoral scanner comprises a body, and a probe at one end of the body, the probe comprising a scanner head. The intraoral scanner further comprises a wireless communication module disposed within the body, and one or more optical sensor to receive light that enters the scanner head and generate intraoral scan data based on the light, wherein the wireless communication module is to wirelessly send the intraoral scan data to a computing device. The intraoral scanner further comprises a primary power source disposed within the body, wherein the primary power source comprises at least one of a long distance wireless power transfer (LDWPT) receiver or a replaceable battery. The intraoral scanner further comprises a secondary power source disposed within the body, wherein the secondary power source comprises at least one of a rechargeable battery or a capacitor.

22 Claims, 14 Drawing Sheets

(51) Int. Cl.
*A61B 1/24* (2006.01)
*A61B 50/13* (2016.01)

(52) U.S. Cl.
CPC ...... *A61B 1/00032* (2013.01); *A61B 1/00045* (2013.01); *A61B 1/24* (2013.01); *A61B 50/13* (2016.02)

(58) Field of Classification Search
CPC ....... A61B 1/24; A61B 50/13; A61B 1/00066; A61B 1/00097; A61B 1/05; A61B 1/0605; A61B 1/128
See application file for complete search history.

(56) References Cited

U.S. PATENT DOCUMENTS

| | | | |
|---|---|---|---|
| 6,334,853 B1 | 1/2002 | Kopelman et al. | |
| 6,463,344 B1 | 10/2002 | Pavlovskaia et al. | |
| 6,542,249 B1 | 4/2003 | Kofman et al. | |
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 11,096,765 B2 | 8/2021 | Atiya et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 11,744,681 B2 | 9/2023 | Kopelman et al. | |
| 11,759,277 B2 | 9/2023 | Shalev et al. | |
| 2009/0298017 A1* | 12/2009 | Boerjes | G06T 1/0007 433/214 |
| 2010/0098269 A1* | 4/2010 | Abolfathi | H04M 1/6066 381/151 |
| 2010/0098270 A1* | 4/2010 | Abolfathi | G01P 1/127 2/463 |
| 2019/0200903 A1* | 7/2019 | Watson | A61B 5/0013 |
| 2019/0269485 A1* | 9/2019 | Elbaz | A61C 9/0053 |
| 2019/0388193 A1 | 12/2019 | Saphier et al. | |
| 2020/0069152 A1* | 3/2020 | Kasumi | G02B 23/24 |
| 2021/0059796 A1 | 3/2021 | Weiss et al. | |
| 2021/0121049 A1 | 4/2021 | Rudnitsky et al. | |
| 2021/0128281 A1 | 5/2021 | Peleg | |
| 2021/0137653 A1 | 5/2021 | Saphier et al. | |
| 2021/0196152 A1 | 7/2021 | Saphier et al. | |
| 2021/0259517 A1* | 8/2021 | Ubbesen | A61B 1/0005 |
| 2022/0280020 A1* | 9/2022 | Hansen | H02J 7/0042 |
| 2023/0000600 A1* | 1/2023 | Wong | G06T 7/0012 |

OTHER PUBLICATIONS

Reissue U.S. Appl. No. 16/784,501; inventor Babayoff, Noam; filed Feb. 7, 2020.
Reissue U.S. Appl. No. 16/784,515; inventor Babayoff, Noam; filed Feb. 7, 2020.
Co-pending U.S. Appl. No. 29/768,525, inventors Ginzburg, Zakhar et al., filed Jan. 29, 2021.
Co-pending U.S. Appl. No. 29/768,563, inventors Ginzburg, Zakhar et al., filed Jan. 29, 2021.

* cited by examiner

Computing
Device
105

Wireless
Connection 207

Charger
292

Cart 290

Scanner
150

Scanner 150

| Light Projector(s) 202 | Camera(s) 204 |

| IMU 206 | Temp. Control Device(s) 208 |

Controller Module 225

Battery Module(s) 222

Charging Module 220

Wireless Communication Module 215

Backup Power Source 272

Wireless Connection 207

Data

Computing Device 105

150

415

405

410

Total Normalized Power

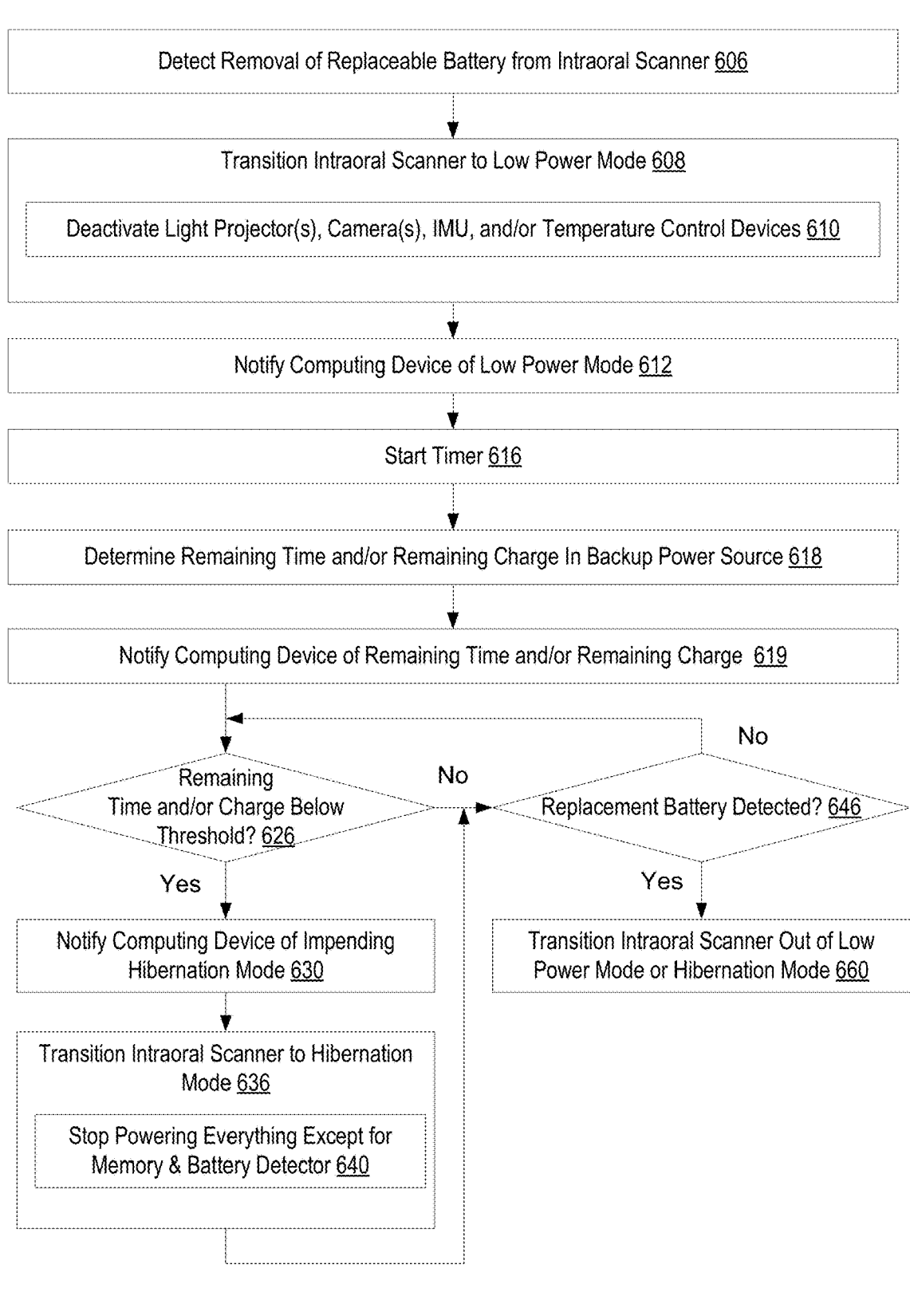

Detect Removal of Replaceable Battery from Intraoral Scanner 606

Transition Intraoral Scanner to Low Power Mode 608

Deactivate Light Projector(s), Camera(s), IMU, and/or Temperature Control Devices 610

Notify Computing Device of Low Power Mode 612

Start Timer 616

Determine Remaining Time and/or Remaining Charge In Backup Power Source 618

Notify Computing Device of Remaining Time and/or Remaining Charge 619

Remaining Time and/or Charge Below Threshold? 626

No

Replacement Battery Detected? 646

No

Yes

Notify Computing Device of Impending Hibernation Mode 630

Yes

Transition Intraoral Scanner Out of Low Power Mode or Hibernation Mode 660

Transition Intraoral Scanner to Hibernation Mode 636

Stop Powering Everything Except for Memory & Battery Detector 640

POWER SOURCES FOR WIRELESS INTRAORAL SCANNERS

RELATED APPLICATIONS

This application claims the benefit under 35 U.S.C. § 119(e) of U.S. Provisional Application No. 63/415,942, filed Oct. 13, 2022, the entire content of which is incorporated by reference herein.

TECHNICAL FIELD

Embodiments of the present disclosure relate to a wireless intraoral scanner and, in particular, to techniques and systems for powering a wireless intraoral scanner.

BACKGROUND

Most intraoral scanners are wired intraoral scanners that are connected to a power source via a wired connection and that are connected to a computing device for data transmission via a wired connection. In many systems, a single wired connection provides both a power connection and a data connection between the intraoral scanner and the computing device.

Wireless intraoral scanners that use a wireless data connection to transmit data to a computing device generally rely on non-replaceable rechargeable batteries to power the intraoral scanners. For busy dental offices, there may be insufficient time to charge the wireless intraoral scanner between patients. As a result, the intraoral scanner may run out of power during intraoral scanning of a patient. Once the intraoral scanner runs out of power, a dentist may then need to charge the intraoral scanner before intraoral scanning can commence. This can result in a need to reschedule a patient visit or to cause a patient visit to take much longer than anticipated, inconveniencing the patient and costing the dentist time and money.

SUMMARY

In a $1^{st}$ implementation, an intraoral scanner comprise a body; a probe at one end of the body, the probe comprising a scanner head; a wireless communication module disposed within the body; one or more optical sensor to receive light that enters the scanner head and generate intraoral scan data based on the light, wherein the wireless communication module is to wirelessly send the intraoral scan data to a computing device; a replaceable battery disposed within the body; a backup power source disposed within the body; and a controller disposed within the body. The controller is to detect removal of the replaceable battery from the body; transition the intraoral scanner into a low power mode; detect insertion of a second replaceable battery into the body; and transition the intraoral scanner out of the low power mode.

A $2^{nd}$ implementation may further extend the $1^{st}$ implementation. In the second implementation the intraoral scanner further comprises: at least one of one or more light projectors, one or more cameras, an inertial measurement unit (IMU), a programmable logic, or one or more temperature control devices; wherein to transition the intraoral scanner into the low power mode the controller deactivates at least one of the one or more light projectors, the one or more cameras, the IMU, the programmable logit, or the one or more temperature control devices; and wherein to transition the intraoral scanner out of the low power mode the controller reactivates at least one of the one or more light projectors, the one or more cameras, the IMU, the programmable logic or the one or more temperature control devices.

A $3^{rd}$ implementation may further extend the $1^{st}$ or $2^{nd}$ implementation. In the $3^{rd}$ implementation the backup power source provides up to about 1 Watt of power for up to about 60 seconds, and wherein the intraoral scanner consumes up to about 1 Watt of power per second while in the low power mode.

A $4^{th}$ implementation may further extend any of the $1^{st}$ through $3^{rd}$ implementations. In the $4^{th}$ implementation the backup power source comprises one or more capacitors.

A $5^{th}$ implementation may further extend any of the $1^{st}$ through $4^{th}$ implementations. In the $5^{th}$ implementation the controller is further to: determine when the replaceable battery reaches a threshold charge level; and output an indicator that the replaceable battery should be replaced responsive to detecting that the replaceable battery has reached the threshold charge level.

A $6^{th}$ implementation may further extend any of the $1^{st}$ through $5^{th}$ implementations. In the $6^{th}$ implementation the controller is further to: initiate a timer responsive to removal of the rechargeable battery from the body, wherein the timer indicates an amount of time remaining before the backup power source is exhausted; and output an indication based on a state of the timer.

A $7^{th}$ implementation may further extend the $6^{th}$ implementations. In the $7^{th}$ implementation the indication changes as the amount of time remaining before the backup power source is exhausted changes.

An $8^{th}$ implementation may further extend any of the $1^{st}$ through $7^{th}$ implementations. In the $8^{th}$ implementation the controller is further to: determine a remaining charge in the backup power source; and output an indication based on the remaining charge.

A $9^{th}$ implementation may further extend any of the $1^{st}$ through $8^{th}$ implementations. In the $9^{th}$ implementation the controller is further to: determine that the backup power source reaches a threshold power level while no rechargeable battery is inserted into the body; and transition the intraoral scanner from the low power mode into a hibernation mode responsive to determining that the backup power source has reached the threshold power level, wherein a first set of components of the intraoral scanner are deactivated during the lower power mode, and wherein a second set of components of the intraoral scanner are deactivated during the hibernation mode, wherein the first set of components is a subset of the second set of components.

A $10^{th}$ implementation may further extend any of the $1^{st}$ through $9^{th}$ implementations. In the $10^{th}$ implementation the controller is further to: determine that the replaceable battery reaches a threshold power level; determine that the intraoral scanner is not in use; and transition the intraoral scanner into a hibernation mode responsive to determining that the replaceable battery has reached the threshold power level and that the intraoral scanner is not in use, wherein a first set of components of the intraoral scanner are deactivated during the lower power mode, and wherein a second set of components of the intraoral scanner are deactivated during the hibernation mode, wherein the first set of components is a subset of the second set of components.

In an $11^{th}$ implementation and intraoral scanning system comprises: an intraoral scanner, comprising: a body; a probe at one end of the body, the probe comprising a scanner head; a wireless communication module disposed within the body; one or more optical sensor to receive light that enters the scanner head and generate intraoral scan data based on the light, wherein the wireless communication module is to wirelessly send the intraoral scan data to a computing device; a replaceable battery disposed within the body; a backup power source disposed within the body; and a controller disposed within the body; the computing device, to wirelessly receive the intraoral scan data; and a second replaceable battery; wherein the controller of the intraoral scanner is to: detect removal of the replaceable battery from the body; transition the intraoral scanner into a low power mode; detect insertion of the second replaceable battery into the body; and transition the intraoral scanner out of the low power mode.

A 12$^{th}$ implementation may further extend the 11$^{th}$ implementation. In the 12$^{th}$ implementation the intraoral scanning system further comprises a battery charger to charge the replaceable battery.

A 13$^{th}$ implementation may further extend the 12$^{th}$ implementation. In the 13$^{th}$ implementation, the intraoral scanning system further comprises: a cart comprising the computing device, a display, and the battery charger.

A 14$^{th}$ implementation may further extend any of the 11$^{th}$ through 13$^{th}$ implementations. In the 14$^{th}$ implementation, the controller is further to transmit, to the computing device, an indicator that the replaceable battery should be replaced responsive to detecting that the replaceable battery has reached a threshold charge level; and the computing device is to output a prompt to replace the replaceable battery to a display.

A 15$^{th}$ implementation may further extend any of the 11$^{th}$ through 14$^{th}$ implementations. In the 15$^{th}$ implementation, the controller is further to transmit, to the computing device, an indicator that the intraoral scanner is in the lower power mode responsive to the intraoral scanner transitioning to the low power mode; and the computing device is to output a prompt that the intraoral scanner is in the low power mode responsive to receiving the indicator.

A 16$^{th}$ implementation may further extend any of the 11$^{th}$ through 15$^{th}$ implementations. In the 16$^{th}$ implementation, the intraoral scanner further comprises at least one of one or more light projectors, one or more cameras, an inertial measurement unit (IMU), or one or more temperature control devices; to transition the intraoral scanner into the low power mode the controller deactivates at least one of the one or more light projectors, the one or more cameras, the IMU, or the one or more temperature control devices; and to transition the intraoral scanner out of the low power mode the controller reactivates at least one of the one or more light projectors, the one or more cameras, the IMU, or the one or more temperature control devices.

A 17$^{th}$ implementation may further extend any of the 11$^{th}$ through 16$^{th}$ implementations. In the 17$^{th}$ implementation, the backup power source provides up to about 1 Watt of power for up to about 60 seconds, and wherein the intraoral scanner consumes up to about 1 Watt of power per second while in the low power mode.

An 18$^{th}$ implementation may further extend any of the 11$^{th}$ through 17$^{th}$ implementations. In the 18$^{th}$ implementation, the backup power source comprises one or more capacitors.

A 19$^{th}$ implementation may further extend any of the 11$^{th}$ through 18$^{th}$ implementations. In the 19$^{th}$ implementation, the controller of the intraoral scanner is further to: determine when the replaceable battery reaches a threshold charge level; and output an indicator that the replaceable battery should be replaced responsive to detecting that the replaceable battery has reached the threshold charge level.

A 20$^{th}$ implementation may further extend any of the 11$^{th}$ through 19$^{th}$ implementations. In the 20$^{th}$ implementation, the intraoral scanner is to send a notice to the computing device responsive to initiation of the low power mode; and the computing device is to: initiate a timer responsive to receipt of the notice, wherein the timer indicates an amount of time remaining before the backup power source is exhausted; and output, to a display, an indication based on a state of the timer.

A 21$^{st}$ implementation may further extend any of the 11$^{th}$ through 20$^{th}$ implementations. In the 21$^{st}$ implementation, the intraoral scanner is to determine a remaining charge in the backup power source and send a notice of the remaining charge to the computing device; and the computing device is to output an indication to a display based on the remaining charge.

A 22$^{nd}$ implementation may further extend any of the 11$^{th}$ through 21$^{st}$ implementations. In the 22$^{nd}$ implementation, the controller of the intraoral scanner is further to: determine that the backup power source reaches a threshold power level while no rechargeable battery is inserted into the body; and transition the intraoral scanner from the low power mode into a hibernation mode responsive to determining that the backup power source has reached the threshold power level, wherein a first set of components of the intraoral scanner are deactivated during the lower power mode, and wherein a second set of components of the intraoral scanner are deactivated during the hibernation mode, wherein the first set of components is a subset of the second set of components.

A 23$^{rd}$ implementation may further extend any of the 11$^{th}$ through 22$^{nd}$ implementations. In the 23$^{rd}$ implementation, the controller of the intraoral scanner is further to: determine that the replaceable battery reaches a threshold power level; determine that the intraoral scanner is not in use; and transition the intraoral scanner into a hibernation mode responsive to determining that the replaceable battery has reached the threshold power level and that the intraoral scanner is not in use, wherein a first set of components of the intraoral scanner are deactivated during the lower power mode, and wherein a second set of components of the intraoral scanner are deactivated during the hibernation mode, wherein the first set of components is a subset of the second set of components.

A 24$^{th}$ implementation may further extend any of the 11$^{th}$ through 23$^{rd}$ implementations. In the 24$^{th}$ implementation, prior to transitioning into the hibernation mode, the intraoral scanner is to send a notice of the hibernation mode to the computing device; and the computing device is to output an indication that the intraoral scanner is in the hibernation mode to a display.

In a 25$^{th}$ implementation, an intraoral scanner comprises: a body; a probe at a first end of the body, the probe comprising a scanner head; a wireless communication module disposed within the body; one or more optical sensor to receive light that enters the scanner head and generate intraoral scan data based on the light, wherein the wireless communication module is to wirelessly send the intraoral scan data to a computing device; a power source disposed within the body; a long distance wireless power transfer (LDWPT) receiver in the body, wherein the LDWPT receiver is configured to power the intraoral scanner based on a wireless power-carrying signal; and a plurality of LDWPT antennas in the body, the plurality of LDWPT antennas connected to the LDWPT receiver and configured to receive the wireless power-carrying signal.

A 26$^{th}$ implementation may further extend the 25$^{th}$ implementation. In the 26$^{th}$ implementation, each of the plurality of LDWPT antennas has a different orientation.

A 27$^{th}$ implementation may further extend the 25$^{th}$ or 26$^{th}$ implementation. In the 27$^{th}$ implementation, the plurality of LDWPT antennas are disposed in the body at a second end of the body that is opposite the first end of the body.

A 28$^{th}$ implementation may further extend any of the 25$^{th}$ through 27$^{th}$ implementations. In the 28$^{th}$ implementation, the LDWPT receiver is configured to receive a power signal at about 24 GHz.

A 29$^{th}$ implementation may further extend any of the 25$^{th}$ through 28$^{th}$ implementations. In the 29$^{th}$ implementation, the power source comprises at least one of a rechargeable battery or a capacitor.

A 30$^{th}$ implementation may further extend any of the 25$^{th}$ through 29$^{th}$ implementations. In the 30$^{th}$ implementation, the power source has a capacity of 2000-3500 mAh.

A 31$^{st}$ implementation may further extend any of the 25$^{th}$ through 30$^{th}$ implementations. In the 31$^{st}$ implementation, the plurality of LDWPT antennas is arranged in an antenna array.

In a 32$^{nd}$ implementation, an intraoral scanning system comprises: a long distance wireless power transfer (LDWPT) transmitter to transmit a wireless power-carrying signal; and an intraoral scanner, comprising: a body; a probe at one end of the body, the probe comprising a scanner head; a wireless communication module disposed within the body; one or more optical sensor to receive light that enters the scanner head and generate intraoral scan data based on the light, wherein the wireless communication module is to wirelessly send the intraoral scan data to a computing device; a power source disposed within the body; a LDWPT receiver in the body, the LDWPT receiver configured to power the intraoral scanner from the wireless power-carrying signal; and a plurality of LDWPT antennas in the body, the plurality of LDWPT antennas connected to the LDWPT receiver and configured to receive the wireless power-carrying signal.

A 33$^{rd}$ implementation may further extend the 32$^{nd}$ implementation. In the 33$^{rd}$ implementation, the intraoral scanning system further comprises the computing device, to wirelessly receive the intraoral scan data, wherein the computing device is connected to the LDWPT transmitter.

A 34$^{th}$ implementation may further extend the 32$^{nd}$ or 33$^{rd}$ implementation. In the 34$^{th}$ implementation, the intraoral scanning system further comprises a cart comprising a computing device, a display, and the LDWPT transmitter.

In a 35$^{th}$ implementation, an intraoral scanning system comprises: a body; a probe at one end of the body, the probe comprising a scanner head; a wireless communication module disposed within the body; one or more optical sensor to receive light that enters the scanner head and generate intraoral scan data based on the light, wherein the wireless communication module is to wirelessly send the intraoral scan data to a computing device; a primary power source disposed within the body, wherein the primary power source comprises at least one of a long distance wireless power transfer (LDWPT) receiver or a replaceable battery; and a secondary power source disposed within the body, wherein the secondary power source comprises at least one of a rechargeable battery or a capacitor.

A 36$^{th}$ implementation may further extend the 35$^{th}$ implementation. In the 36$^{th}$ implementation, the primary power source comprises the replaceable battery, the intraoral scanner further comprising: a controller disposed within the body, wherein the controller is to: detect removal of the replaceable battery from the body; transition the intraoral scanner into a low power mode; detect insertion of a second replaceable battery into the body; and transition the intraoral scanner out of the low power mode.

A 37$^{th}$ implementation may further extend the 35$^{th}$ or 36$^{th}$ implementation. In the 37$^{th}$ implementation, the primary power source comprises the LDWPT receiver, and wherein the secondary power source is to power the intraoral scanner while a wireless power-carrying signal to the intraoral scanner is interrupted.

BRIEF DESCRIPTION OF THE DRAWINGS

Embodiments of the present disclosure are illustrated by way of example, and not by way of limitation, in the figures of the accompanying drawings.

FIG. 6 illustrates a flow diagram for a method of power conservation for an intraoral scanner, in accordance with embodiments of the present disclosure.

DETAILED DESCRIPTION

Described herein are embodiments of a wireless intraoral scanner that can be used indefinitely (e.g., that avoids downtime and/or can be used with unlimited scanning time). In embodiments, the intraoral scanner includes a replaceable battery and a backup power source. The intraoral scanner may notify a user when the intraoral scanner reaches a threshold minimal power level (e.g., when the intraoral scanner is about to run out of power). A user may then remove the replaceable battery and insert a new replaceable battery without the intraoral scanner losing power. While the replaceable battery is being replaced, the intraoral scanner may rely on the backup power source for power. In some embodiments, the intraoral scanner enters a lower power mode once the replaceable battery is removed, and exits the low power mode once a new replaceable battery is inserted into the intraoral scanner. The low power mode may shut down unnecessary components to prolong the amount of time that the backup power source can power the intraoral scanner. Accordingly, by using the low power mode the intraoral scanner provides a user with more time to swap out the replaceable battery.

In some embodiments, the wireless intraoral scanner includes a long distance wireless power transfer (LDWPT) receiver, one or more LDWPT antennas and a backup power source. The LDWPT receiver may receive a wireless power-carrying signal and use the wireless power-carrying signal to power the intraoral scanner under most circumstances. Occasionally an obstruction may be interposed between an LDWPT transmitter and all of the LDWPT antennas of the intraoral scanner. During such obstruction, the intraoral scanner may rely on the backup power source to continue powering the intraoral scanner. Once the obstruction is gone, the intraoral scanner may resume powering itself via the power-carrying signal received by the LDWPT antennas. The intraoral scanner may additionally recharge the backup power source at this time so that the backup power source is ready for the next time an obstruction blocks the wireless power-carrying signal from reaching the LDWPT receiver.

In some embodiments, a wireless intraoral scanner includes a replaceable battery and an LDWPT receiver (together with one or more LDWPT antennas). The wireless intraoral scanner may additionally include an additional backup power source. The wireless intraoral scanner may be powered by the replaceable battery or via the LDWPT receiver. The LDWPT receiver may power the intraoral scanner during replacement of the replaceable battery.

Embodiments discussed herein enable continuous use of an intraoral scanner. Accordingly, the wireless intraoral scanners described herein can be used without pausing to charge the wireless intraoral scanners.

Figure 1:
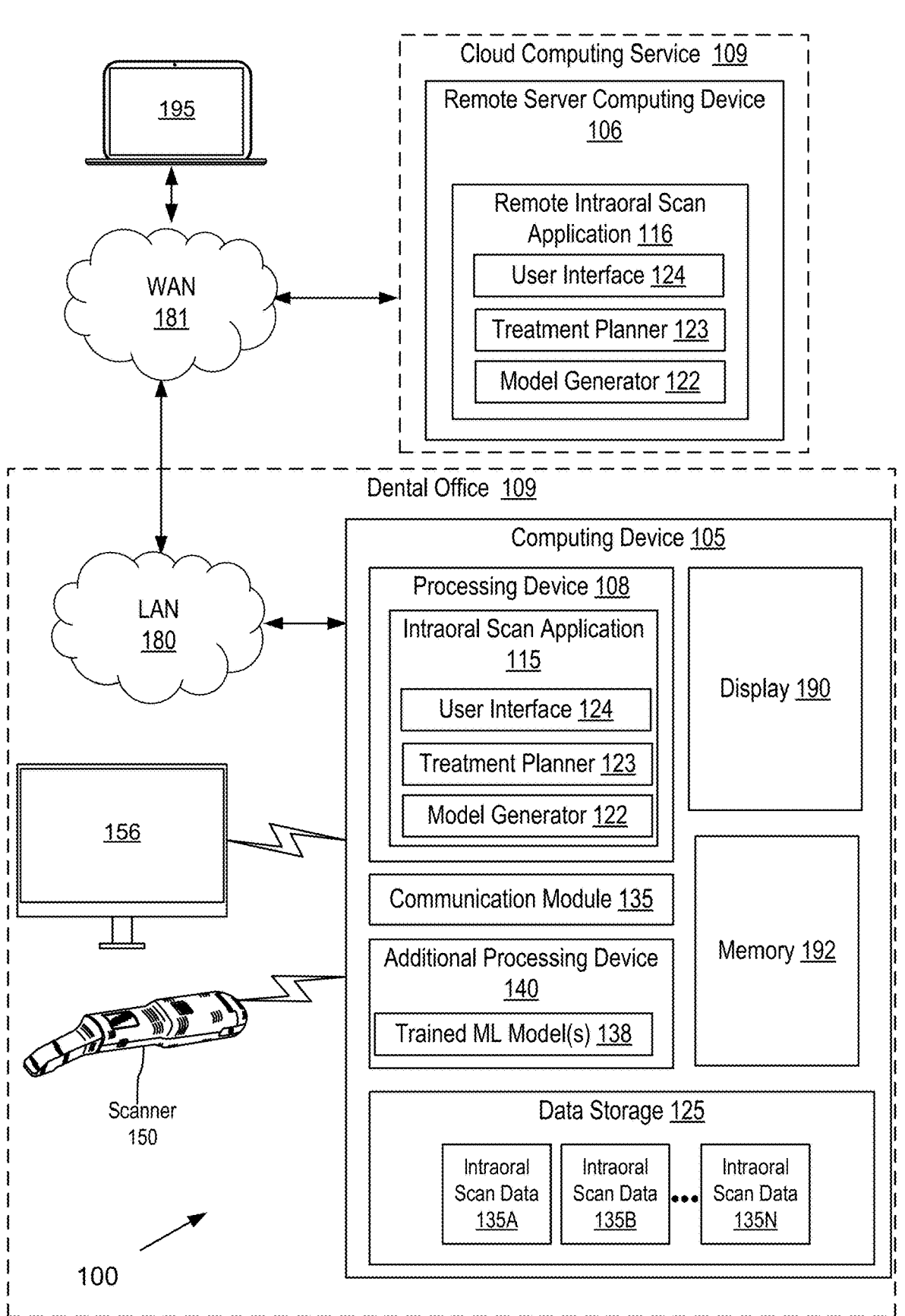
FIG. 1 illustrates an intraoral scanning system, in accordance with embodiments of the present disclosure.

FIG. 1 illustrates an intraoral scanning system 100, in accordance with an embodiment. Intraoral scanning system 100 may include only components located at a single location (e.g., at a dentist office 109 or a dental lab) in embodiments. The intraoral scanning system 100 at a minimum includes a wireless intraoral scanner (also referred to simply as a scanner) 150 and a computing device 105. In some embodiments, the intraoral scanning system 100 may additionally include, or take advantage of, a display 156 and/or a local area network (LAN) 180. Via the LAN 180, the intraoral scanning system 100 (e.g., the computing device 105) may connect to a wide area network (WAN) 181, and through the WAN 181 to a remote server computing device 106. The LAN 180 may include a router, switch, bridge and/or other network device (not shown) that enables communication between multiple devices (e.g., computing device 105 and scanner 150) connected to the LAN 180. The network device may provide wired connections to the LAN using, for example, Ethernet ports, universal serial bus (USB) ports and/or Firewire® ports. The network device may additionally provide wireless connections to the LAN using, for example, a Wi-Fi transceiver.

The WAN 181 may include a public WAN (e.g., the Internet), a private WAN (e.g., an intranet), or a combination thereof. The WAN 181 may include or connect to remote server computing device 106. The server computing device 106 may include a physical machine and/or a virtual machine hosted by a physical machine. The physical machine may be a rackmount server, a desktop computer, or other computing device. In one embodiment, the remote server computing device 106 includes a virtual machine managed and provided by a cloud provider system or cloud computing service 109. Each virtual machine offered by a cloud service provider may be hosted on a physical machine configured as part of a cloud. Such physical machines are often located in a data center. The cloud provider system and cloud may be provided as an infrastructure as a service (IaaS) layer. One example of such a cloud is Amazon's® Elastic Compute Cloud (EC2®).

In some embodiments, computing device 105 connects to scanner 150 wirelessly via a wireless protocol. The connection may be an indirect connection via LAN 180 or may be a direct connection between computing device 105 and scanner 150. For example, scanner 150 may pair with and communicate wirelessly with computing device 105 using a wireless protocol.

Computing device 105 may include a processing device 108, a communication module 135, a memory 192, and/or a data storage 125. In some embodiments, memory 192 and data storage 125 are combined. In some embodiments, the processing device 108, communication module 135, memory 192 and/or data storage 125 are components of a system on a chip (SoC).

The processing device 108 may be or include a micro-controller, a DSP, a PLC, a microprocessor or programmable logic device such as an FPGA or a CPLD. The processing device 108 may additionally or alternatively include one or more special purpose processor and/or general purpose processor, such as a complex instruction set computing (CISC) microprocessor, reduced instruction set computing (RISC) microprocessor, very long instruction word (VLIW) microprocessor, processor implementing other instruction sets, or processor implementing a combination of instruction sets. Examples of special-purpose processing devices include an application specific integrated circuit (ASIC), a field programmable gate array (FPGA), a digital signal processor (DSP), and network processor. Processing device 108 is configured to execute a intraoral scan application 115 in embodiments.

The memory may include a non-volatile memory (e.g., RAM) and/or a volatile memory (e.g., ROM, Flash, etc.). The data storage 125 may include a local data store and/or a remote data store. The data storage 125 may be or include secondary storage, such as a disc drive, a solid state drive, and so on. Computing device 105 may additionally include a display 190 and/or one or more additional processing device 140 in some embodiments.

The communication module 135 enables the computing device 105 to connect to a LAN and/or directly to other devices such as scanner 150. The communication module 135 may be configured to manage security, manage sessions, manage communications with external devices, and so forth. In one embodiment, the communication module 135 is configured to wirelessly communicate using Wi-Fi®. Alternatively, or additionally, the communication module may be configured to communicate using Bluetooth®, Zigbee®, Internet Protocol version 6 over Low power Wireless Area Networks (6LowPAN), power line communication (PLC), Ethernet (e.g., 10 Megabyte (Mb), 100 Mb and/or 1 Gigabyte (Gb) Ethernet) or other communication protocols.

In some embodiments, computing device 105 includes one or more additional processing device 140. The additional processing device 140 may be a specialized processing device that is optimized for execution of trained machine learning models. Additional processing device 140 may execute one or more trained machine learning (ML) models 138, which may include models for identifying (e.g., on a point, patch or pixel level) moving tissue, foreign objects, excess tissue, soft tissue, hard tissue, and so on. Outputs of the trained machine learning model(s) 138 may be provided to intraoral scan application 115, which may use such outputs to perform one or more actions. Examples of trained machine learning models 138 that may execute on the additional processing device 140 are described in U.S. Pat. No. 11,367,192, issued Jun. 21, 2022, and entitled "Foreign Object Filtering for Intraoral scanning" and U.S. Pat. No. 11,238,586, issued Feb. 1, 2022, and entitled "Excess Material Removal Using Machine learning, which are each incorporated by reference herein in their entirety.

In some embodiments, computing device 105 is a desktop computing device. In some embodiments, computing device 105 is a laptop or notebook computing device. In some embodiments, computing device 105 is a component of a cart used for intraoral scanning.

In some embodiments, computing device 105 includes a display 190. The display 190 may be an integrated or attached display 190. Computing device may alternatively or additionally be connected to a display 156. Display 190 and display 156 may be, for example, a liquid crystal display (LCD), an organic light emitting diode (OLED) display, a cathode ray tube (CRT) display, or other type of display. Display 156 may be, for example, a television (e.g., smart TVs), computer monitor, mobile device that includes a display (e.g., mobile phones, laptop computers, tablet computers, etc.), augmented reality (AR) headset, mixed reality (MR) headset, and so on. Some displays 156 may be physically connected to the computing device 105 via a wired connection. Some displays 156 may be wirelessly connected to computing device 105 via a wireless connection, which may be a direct wireless connection or a wireless connection via a wireless network. In embodiments, display 156 is a smart display such as a smart television (TV). A smart TV may include an application installed thereon for communicating with and/or acting as a remote display for computing device 105. Alternatively, or additionally, a smart TV may include a web browser, which may be used to navigate to a web page that streams data from computing device 105. For example, the web page may stream a user interface of intraoral scan application 115.

In embodiments, intraoral scanner 150 is a wireless intraoral scanner that includes multiple internal power sources. In one embodiment, intraoral scanner 150 includes a replaceable battery and a secondary power source, such as a secondary rechargeable battery or one or more capacitor. In one embodiment, intraoral scanner includes an LDWPT receiver and an additional power source (e.g., a rechargeable battery). Various power source options for the intraoral scanner 150 are discussed below with reference to FIGS. 2A-3B.

In embodiments, intraoral scanner 150 is wirelessly connected to computing device 105. In one embodiment, scanner 150 is wirelessly connected to computing device 105 via a direct wireless connection. In one embodiment, scanner

150 is wirelessly connected to computing device 105 via a wireless network (e.g., LAN 180). In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, computing device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router.

Intraoral scanner 150 may be a wireless handheld device that is not tethered to a computer, display, and/or other hardware. The intraoral scanner 150 may be used to perform intraoral scanning of a patient's oral cavity.

Intraoral scanner 150 may include one or more light source, optics and one or more detectors for generating intraoral scan data (e.g., intraoral scans, color images, NIRI images, etc.), one or more buttons and/or touch sensitive inputs (e.g., touch pads and/or touchscreens), and so on. Intraoral scanner 150 may additionally include a memory and/or a processing device (e.g., a controller) for performing initial processing on some or all of the intraoral scan data before it is transmitted to computing device 105. Scanner 150 may additionally include a communication module (e.g., a wireless communication module) such as a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols. Alternatively, the scanner 150 may connect to a wide area network (WAN) such as the Internet, and may connect to the computing device 105 and/or remote server computing device 106 via the WAN. One example of a scanner 150 is the iTero® intraoral digital scanner manufactured by Align Technology, Inc. Another example of a scanner 150 is set forth in U.S. Publication No. 2019/0388193, filed Jun. 19, 2019, which is incorporated by reference herein. Two example scanners are described in greater detail below with reference to FIGS. 9-10.

In embodiments, the scanner 150 may include a wireless communication module, one or more rechargeable battery, one or more replaceable battery (which may or may not be rechargeable), a charging module for charging the one or more rechargeable battery and/or a controller (e.g., a processing device) for controlling one or more functions of the scanner 150, among many other components, some of which are discussed herein below.

In addition to or instead of including a wireless communication module, scanner 150 may include an Ethernet network interface controller (NIC), a universal serial bus (USB) port, a parallel port, a serial port, or other wired port. In some embodiments, the NIC or port may connect the scanner 150 to a computing device 105 via a wired connection. In embodiments, the scanner 150 may additionally or alternatively include any of the components of the intraoral scanners described with reference to FIGS. 9-10.

Intraoral scanner 150 may generate intraoral scans, which may be or include color and/or monochrome 3D information, and send the intraoral scans to computing device 105 via the wireless connection. In some embodiments, intraoral scans include height maps. Intraoral scanner 150 may additionally or alternatively generate color two-dimensional (2D) images (e.g., viewfinder images), and send the color 2D images to computing device 105 via the wireless connection. Scanner 150 may additionally or alternatively generate 2D or 3D images under certain lighting conditions, such as under conditions of infrared or near-infrared (NIRI) light and/or ultraviolet light, and may send such 2D or 3D images to computing device 105 via the wireless connection. Intraoral scans, color images, and images under specified lighting conditions (e.g., NIRI images, infrared images, ultraviolet images, etc.) are collectively referred to as intraoral scan data 135A-N. An operator may start recording scans with the scanner 150 at a first position in the oral cavity, move the scanner 150 within the oral cavity to a second position while the scans are being taken, and then stop recording the scans. In some embodiments, recording may start automatically as the scanner 150 identifies teeth and/or other objects.

A intraoral scan application 115 running on processing device 108 of computing device 105 may wirelessly communicate with the scanner 150 via communication module 135 to effectuate an intraoral scan. A result of the intraoral scan may be intraoral scan data 135A, 135B through 135N that may include one or more sets of intraoral scans, one or more sets of viewfinder images (e.g., color 2D images showing a field of view of the intraoral scanner), one or more sets of NIRI images, and so on. Each intraoral scan may be a two-dimensional (2D) or 3D image that includes a height information (e.g., a height map) of a portion of a dental site, and thus may include x, y and z information. In one embodiment, each intraoral scan is a point cloud. In one embodiment, the intraoral scanner 150 generates numerous discrete (i.e., individual) intraoral scans and/or additional images. In some embodiments, sets of discrete intraoral scans may be merged into a smaller set of blended intraoral scans, where each blended scan is a combination of multiple discrete intraoral scans.

In embodiments, scanner 150 generates and sends to computing device 105 a stream of intraoral scan data. The stream of intraoral scan data may include separate streams of intraoral scans, color images and/or NIRI images (and/or other images under specific lighting conditions) in some embodiments. In one embodiment, a stream of blended intraoral scans is sent to computing device 105. In embodiments, the color 2D images in the stream are generated at a first frame rate.

In some embodiments, scanner 150 compresses intraoral scan data (e.g., intraoral scans, color images, NIRI images, etc.) prior to sending the intraoral scan data to computing device 105. In some embodiments, video compression techniques (e.g., optionally based on H.264 codec) are used to compress the stream of intraoral scan data. In some embodiments, intraoral scan data is compressed by a factor of 20 to 40. Accordingly, similarities between sequentially generated scans/images may be used to reduce the amount of data sent for each scan/image. For example, scanner 150 may determine a delta or difference between a previously sent scan and a current scan, and may send over the delta or difference rather than the scan or image. This may significantly reduce an amount of information sent over the wireless connection. Scanner 150 may include an onboard (e.g., internal) processing device that performs compression of at least some of the intraoral scan data.

In some embodiments, scanner 150 does not send whole scans and/or whole images to computing device 105. In one embodiment, scanner 150 may perform one or more computations on the intraoral scan data (e.g., intraoral scans, color images, NIRI images, etc.) to determine one or more areas of interest (AOIs) within the intraoral scan data. The one or more computations may be performed using trained machine learning models that are optimized for resource constrained devices and/or using one or more image processing algorithms. Scanner 150 may then perform data reduction such as by cropping the intraoral scans, images, etc. such that areas outside of the AOIs are cropped out of the scans/images and/or by reducing a resolution of areas outside of the AOIs. Scanner 150 may include an onboard processing device (e.g., a controller or other processing device) that can perform the one or more computations and/or data reduction/cropping of the scan data. The cropped or reduced scans/images are then sent to computing device 105. This, in addition to or instead of performing compression on the intraoral scan data, can reduce a total bandwidth associated with sending intraoral scan data to computing device 105. In one embodiment, AOIs are determined for intraoral scans, and intraoral scans are cropped or reduced before sending to computing device 105, but whole color images such as color viewfinder images are sent to computing device 105 without first cropping or reducing the color images. The uncropped viewfinder image may be presented to a doctor/dentist during the scanning process to show a current field of view of the scanner 150.

Computing device 105 receives intraoral scan data from scanner 150, then stores the intraoral scan data 135A-N in data storage 125. If the intraoral scan data has been compressed, computing device 105 may decompress the intraoral scan data before it is stored. Alternatively, computing device 105 may store the intraoral scan data in a compressed state, and may decompress the intraoral scan data before processing it. In some embodiments, only some of the intraoral scan data is stored (e.g., just the intraoral scans may be stored).

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan/image data sets, each of which may include 2D intraoral scans/images and/or 3D intraoral scans/images of particular teeth and/or regions of an intraoral site. In one embodiment, separate scan/image data sets are created for the maxillary arch, for the mandibular arch, for a patient bite, and for each preparation tooth. Alternatively, a single large intraoral scan/image data set is generated (e.g., for a mandibular and/or maxillary arch). Such scans/images may be provided from the scanner to the computing device 105 in the form of one or more points (e.g., one or more pixels and/or groups of pixels). For instance, the scanner 150 may provide such a 3D scan/image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

During an intraoral scan session, intraoral scan application 115 receives and processes intraoral scan data (e.g., intraoral scans) and generates a 3D surface of a scanned region of an oral cavity (e.g., of a dental site) based on such processing. To generate the 3D surface, intraoral scan application 115 may register and "stitch" or merge together the intraoral scans generated from the intraoral scan session in real time or near-real time as the scanning is performed. In one embodiment, performing registration includes capturing 3D data of various points of a surface in multiple scans (views from a camera), and registering the scans by computing transformations between the scans. The 3D data may be projected into a 3D space for the transformations and stitching. The scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans and/or reduced or cropped scans. Registration algorithms are carried out to register two or more adjacent intraoral scans and/or to register an intraoral scan with an already generated 3D surface, which essentially involves determination of the transformations which align one scan with the other scan and/or with the 3D surface. Registration may involve identifying multiple points in each scan (e.g., point clouds) of an scan pair (or of a scan and the 3D model), surface fitting to the points, and using local searches around points to match points of the two scan (or of the scan and the 3D surface). For example, intraoral scan application 115 may match points of one scan with the closest points interpolated on the surface of another image, and iteratively minimize the distance between matched points. Other registration techniques may also be used. Intraoral scan application 115 may repeat registration and stitching for all scans of a sequence of intraoral scans and update the 3D surface as the scans are received.

In one embodiment, the scanner 150 is used as an input device to control the view of the 3D surface of a dental site. Embodiments of the present invention enable a user to perform operations (such as to control or navigate a user interface of intraoral scan application 115 and/or to manipulate medical images or a representation generated from medical images) while still engaged with a patient. Scanner 150 may include one or more buttons, one or more touch sensitive inputs (e.g., touch pads and/or touchscreens) and/or an inertial measurement unit (IMU) including one or more inertial measurement devices (e.g., accelerometers and/or gyroscopes) that may be used to navigate the user interface of the intraoral scan application 115 and/or manipulate a generated 3D surface.

A user (e.g., a practitioner) may navigate through scanning segments (e.g., an upper dental arch segment, a lower dental arch segment, a bite segment, and optionally a separate segment for each preparation tooth) via a user interface (UI) of the intraoral scan application 115 by various input devices, such as a cursor control device (e.g., a mouse), a remote control (e.g., of a smart TV), a touch input device (e.g., touchscreen) of a scanner 150, etc. In embodiments, a scanner 150 may allow the user to easily navigate or control the user interface of the intraoral scan application 115 using the touch input and/or buttons of the scanner 150. For example, the user may utilize a combination of buttons and various touch gestures on the touch sensor of the scanner 150 to navigate the intraoral scan application 115. In some embodiments, intraoral scanner 150 includes a touchscreen that outputs one or more virtual buttons. A user may interact with the one or more virtual buttons (e.g., by pressing a virtual button) to send a control signal to the intraoral scan application 115. Which virtual buttons are displayed on the intraoral scanner's 150 touchscreen may depend on a current mode of the intraoral scan application 115.

Navigation or control of the user interface of the intraoral scan application 115 may be performed via user input. The user input may be performed through various devices, such as a touch input device (e.g., a touchscreen), keyboard, mouse, or other similar control devices of one or more device wirelessly connected to computing device 105. User input may also be provided via scanner 150 in embodiments, such as via a touchpad and/or touchscreen of the intraoral scanner 150. Navigation of the user interface may involve, for example, navigating between various modules or modes, navigating between various segments, controlling the viewing of the 3D rendering, or any other user interface navigation. A touch sensitive scanner (e.g., which may include a touchscreen) allows the user to navigate or control the user interface without continuously disengaging from the patient.

In one embodiment, intraoral scan application 115 includes a touch input module (not shown) that receives and interprets touch input data from scanner 150. Scanner 150 may receive different types of touch input such as hold gestures, swipe gestures, tap gestures, circular gestures, and so on. Additionally, or alternatively, a touchscreen of the intraoral scanner 150 may display multiple different virtual buttons, and user interaction with each of the virtual buttons may trigger a different action in intraoral scan application 115. The touch input module may determine a type of touch gesture that a user performed based on the received touch input and/or what virtual button was pressed based on a detected finger. The touch input module may then initiate functions or operations of the user interface (or intraoral scan application generally) responsive to the determined touch gesture. The functions or operations that are initiated may depend both on the current mode of the intraoral scan application 115 and the determined touch gesture and/or pressed virtual button. Accordingly, the same touch gesture or finger interaction with a same region of the touchscreen may cause a first function to be performed in a first mode of the intraoral scan application and may cause a second function to be performed in a second mode. Specific modes of operation and touch gestures and/or virtual buttons that initiate operations or functions for those modes are discussed in greater detail below.

In one embodiment, computing device 105 executing intraoral scan application 115 receives a touch input from a touch sensor (e.g., a touchpad or touchscreen) of scanner 150 (e.g., which may include a press of a virtual button on a touchscreen) and/or a button press from a button of scanner 150 during an intraoral scan session. In one embodiment, intraoral scan application 115 determines whether the touch input is a hold gesture or a swipe gesture. The computing device may then perform a first function or operation to control a user interface of the intraoral scan application if the touch input is a hold gesture (or a particular button of virtual button is depressed) and a second function or operation to control the user interface of the intraoral scan application if the touch input is a swipe gesture (or another button or virtual button is depressed). Examples of functions that may be performed include activating a gyroscope in the intraoral scanner 150, using data from the gyroscope to control an orientation of a virtual 3D surface (e.g., if a hold gesture is detected) and proceeding to next or previous scan segments (e.g., if a swipe gesture is detected). The functions or operations performed responsive to the hold or swipe gestures and/or responsive to a user pressing a virtual button of a touchscreen on the intraoral scanner 150 may be functions that traditionally are performed responsive to a user using a keyboard, mouse and/or touchscreen of a computer. Results of the inputs from the scanner 150 (e.g., button pushes, virtual button pushes, swipe gestures, hold gestures, movement of the scanner 150, etc.) may cause one or more menus or options of the intraoral scan application 115 to be navigated or transitioned between, and/or an updated menu or options to be output to a display 156, 190 associated with the intraoral scanner 150 and/or to a touchscreen of the intraoral scanner 150. In some embodiments, pressing a particular button or buttons (including one or more virtual buttons of a touchscreen) or performing a hold gesture of a touch sensitive input causes intraoral scan application 115 to output a navigation overlay to a display 156, 190. While and/or after the button(s) and/or virtual buttons are pushed and/or during the hold gesture of the touch sensitive input, a user may move the scanner 150 and motion of the scanner may be used as an input to navigate the navigation overlay. For example, the scanner 150 may be moved left to select a first menu option (e.g., switch to previous scan segment), right to select a second menu option (e.g., switch to next scan segment), up to select a third menu option or down to select a fourth menu option. The movement of the scanner may register as an input that causes a user interface of the intraoral scan application 115 to be updated, and the updated user interface may be output to the display 156, 190 associated with scanner 150.

By providing touch sensors, touchscreens and/or buttons in the intraoral scanner 150 and an intraoral scan application 115 that can respond to touch input from such touch sensors, that can respond to input from touchscreens (e.g., presses of virtual buttons displayed on a touchscreen) and/or that can respond to use of the buttons, embodiments improve the efficiency of performing intraoral scans. Additionally, display 156 may not include an input device for controlling intraoral scan application 115. However, scanner 150 may function as such an input device for controlling intraoral scan application 115. For example, if the intraoral scan application 115 is outputting image data to display 156, then a user of scanner 150 may press a physical button, press a virtual button of a touchscreen on the intraoral scanner 150 and/or use a hold gesture on a touch input of the scanner 150 to activate a view mode. During the view mode, the user may move the scanner and/or interface with the touchscreen or touch pad on the intraoral scanner 150 to rotate a view of a 3D surface or 3D model of a dental site. The user may release the button, virtual button or hold gesture to resume a scanning mode and continue generating intraoral scans. Alternatively, the user may press a different virtual button to resume the scanning mode and continue generating intraoral scans.

When a scan session is complete (e.g., all scans for an intraoral site or dental site have been captured), intraoral scan application 115 may send the intraoral scan data (e.g., including at a minimum intraoral scans) to remote server computing device 106 for processing by remote intraoral scan application 116. Remote intraoral scan application 116 may include a model generator 122 that may process the intraoral scan data to generate one or more virtual 3D model of a patient's dental arch or dental arches. Additionally, or alternatively, intraoral scan application may include model generator 122. Model generator 122 may generate a virtual 3D model (also referred to as a digital 3D model) of one or more scanned dental sites. The virtual 3D model includes a 3D surface of the one more scanned dental sites. To generate the virtual 3D model, model generator 122 may register and "stitch" or merge together the intraoral scans generated from the intraoral scan session. In one embodiment, registration is performed for adjacent and/or overlapping intraoral scans (e.g., each successive frame of an intraoral video). In one embodiment, registration is performed using blended scans and/or reduced or cropped scans. Registration algorithms may be carried out to register two or more adjacent intraoral scans and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, model generator 122 may match points of one scan with the closest points interpolated on the surface of another scan, and iteratively minimize the distance between matched points. Other registration techniques may also be used. The registration and stitching that are performed to generate the 3D model may be more accurate than the registration and stitching that are performed to generate the 3D surface that is shown in real time or near-real time during the scanning process.

Model generator 122 may repeat registration for all scans of a sequence of intraoral scans to obtain transformations for each scan, to register each scan with the previous one and/or with a common reference frame (e.g., with the 3D model). Model generator 122 may integrate all scans (or all scans associated with a segment) into a single virtual 3D model by applying the appropriate determined transformations to each of the scans. Each transformation may include rotations about one to three axes and translations within one to three planes. In some embodiments, a first model of an upper dental arch and a second model of a lower dental arch are generated.

In some embodiments, intraoral scan application 115 includes a local version of model generator 122, which can generate virtual 3D models of dental arches locally on computing device 105.

A user (e.g., a dentist) may access and view the virtual 3D model(s) by accessing a user interface 124 of remote intraoral scan application 116 from a client computing device 195. Alternatively, a user may access and view the virtual 3D models by interfacing with computing device 105. The client computing device 195 may be any computing device, such as a tablet computer, a desktop computer, a mobile phone, a laptop, a notebook computer, and so on.

User interface 124 of remote intraoral scan application 116 or of intraoral scan application 115 may generate a view of the 3D model and output the view to client computing device 195 for display of the 3D model to a user (e.g., a doctor) via a display of the client computing device 195. A doctor may then interface with the client computing device 195 or computing device 105 to generate commands to change the view of the 3D model (e.g., by zooming in or out, panning, rotating, etc.). The client computing device 195 may send the command to remote intraoral scan application 116, which may change the view of the 3D model, and then send the updated view to the client computing device 195. Alternatively, a user may provide commands to computing device 105 for changing a view of a 3D model. In this manner, the 3D model can be checked visually by the doctor. The doctor can virtually manipulate the 3D model via the user interface of the client computing device 195 or computing device 105 with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model).

In one embodiment, remote intraoral scan application 116 and/or intraoral scan application 115 includes a treatment planner 123 configured to perform treatment planning for orthodontic treatment and/or prosthodontic treatment. In some embodiments, processing device 108 includes a local version of treatment planner 123 and/or user interface 124. Treatment planner 123 may additionally perform dental diagnostics and/or prognostics. Via the user interface 124, a practitioner may view one or more of the upper dental arch, the lower dental arch, a particular preparation tooth and/or the patient bite, each of which may be considered a separate scan segment or mode. The treatment planner 123 in embodiments generates an orthodontic treatment plan, including a 3D model for a final tooth arrangement and 3D models for one or more intermediate tooth arrangements. Treatment planner 123 may additionally or alternatively perform diagnostics of a patient's oral cavity and/or provide a prognosis of one or more dental conditions and/or suggested treatments for the one or more dental conditions. The treatment planner 123 may further perform one or multiple different analyses of the patient's dental arches and/or bite. The analyses may include an analysis for identifying tooth cracks, an analysis for identifying gum recession, an analysis for identifying tooth wear, an analysis of the patient's occlusal contacts, an analysis for identifying crowding of teeth (and/or spacing of teeth) and/or other malocclusions, an analysis for identifying plaque, an analysis for identifying tooth stains, an analysis for identifying caries, and/or other analyses of the patient's dentition. Once the analyses are complete, a dental diagnostics summary and/or detailed dental diagnostics information optionally including prognosis and/or treatment options may be presented to a client computing device 195 and/or via display 156, 190. A doctor may control the treatment planner 123 and navigate menus and options of the treatment planner using the client computing device 195, computing device 105 and/or scanner 150.

Once an adequate set of 3D models is generated, the 3D models may be saved to the patient profile. The dental practitioner may then navigate to a delivery mode to electronically send the completed patient profile to a processing center. The processing center may then generate the custom made series of clear aligners for the patient and deliver the clear aligners to the dental practitioner. The patient would then return to the dental practitioner to receive the first set of clear aligners and verify the clear aligners properly fit onto the patient's teeth.

Figure 2A:
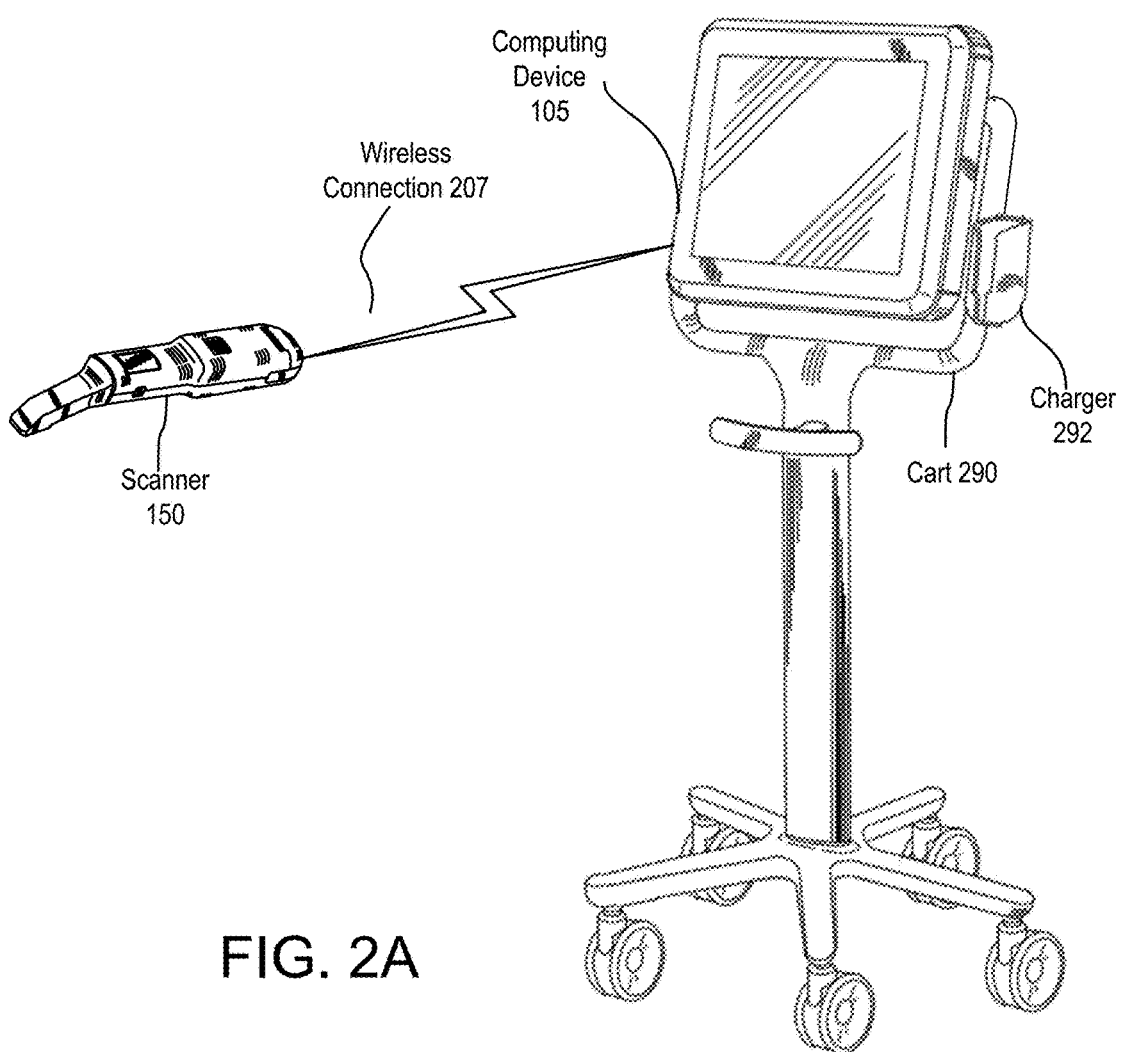
FIGS. 2A-B illustrate an intraoral scanner with a replaceable battery wirelessly connected to a computing device via a wireless connection, in accordance with embodiments of the present disclosure.
Figure 2B:
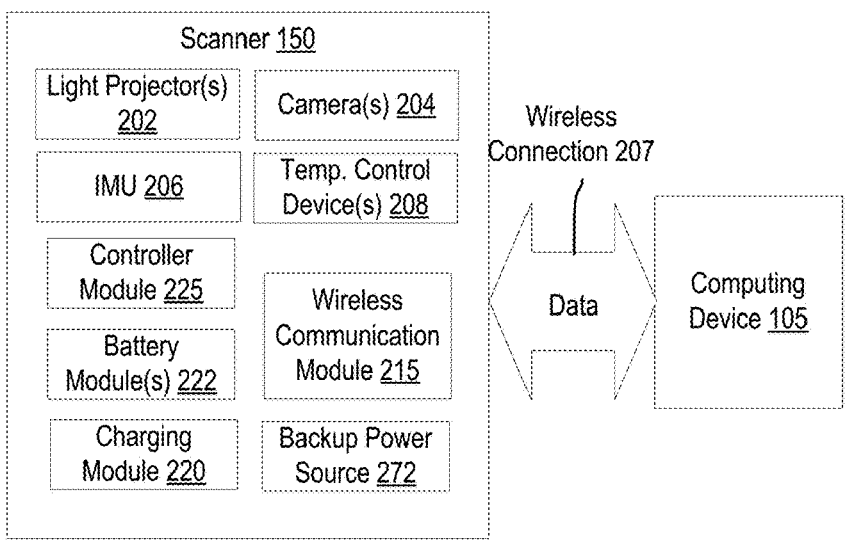

FIGS. 2A-3B illustrate examples of different wireless intraoral scanning systems according to embodiments. FIGS. 2A-B illustrate an intraoral scanner with a replaceable battery wirelessly connected to a computing device via a wireless connection, in accordance with embodiments of the present disclosure.

Scanner 150 in one embodiment includes one or more light projectors 202, one or more cameras 204 (e.g., image capture devices such as charge coupled devices (CCDs) and/or complementary metal-oxide-semiconductor (CMOS) devices), an inertial measurement unit (IMU) 206, one or more temperature control devices 208 (e.g., heaters, fans, coolant systems, etc.), actuators (not shown), and/or other components such as those discussed with reference to FIGS. 9-10. In embodiments, the IMU 206 may include one or more accelerometers, gyroscopes, micro-electro-mechanical systems (MEMS) devices for measuring motion and/or inertia, and so on. Scanner 150 may additionally or alternatively include a controller module 225, one or more battery modules 222 (e.g., a replaceable battery module and/or an integrated rechargeable battery module), a charging module 220, a wireless communication module 215 and/or a backup power source 272.

Wireless communication module 215 may include a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols.

Battery modules 222 may include an integrated rechargeable battery module that includes one or more removable and replaceable rechargeable battery. The rechargeable battery may include a lithium-ion battery, for example. Battery modules 222 may additionally or alternatively include a replaceable battery module that can receive non-rechargeable batteries. Accordingly, battery modules 222 may include just one or more rechargeable batteries, just one or more replaceable batteries, or both one or more rechargeable batteries and one or more replaceable batteries.

Backup power source 272 may be a non-replaceable power source, and may sustain many (e.g., thousands of)

charging/discharging cycles. In one embodiment, backup power source 272 is a rechargeable battery, such as a lithium-ion battery. In one embodiment, backup power source 272 comprises one or more capacitors, such as a bank of capacitors. In one embodiment, backup power source 272 includes one or more super-capacitors. In embodiments, backup power source 272 is configured to provide up to about 1 W (e.g., up to 1 W) of power for at least about 45 seconds (e.g., for at least 45 seconds, for at least 60 seconds, etc.). In one embodiment, backup power source 272 contains 2-4 (e.g., 3) capacitors each having 5 mWh of stored energy. Accordingly, in embodiments backup power source 272 can provide 1 W of power consumption with a 1V cutoff voltage for a threshold period of time.

Charging module 220 may include a charger for charging a rechargeable battery in a battery module 222. The charging module 220 may include a traditional charger that receives a current via a wired connection. The charging module 220 may additionally or alternatively include an inductive or wireless charger component that includes a secondary coil configured to inductively couple with a primary coil of an external wireless charger that is external to the scanner 150 (e.g., that is integrated into a cradle for the scanner 150).

Controller module 225 may include a processing device, memory, and/or other components for controlling one or more operations of scanner 150. In one embodiment, controller module 225 includes a system on a chip (SoC) including a processor and memory. In one embodiment, controller module 225 includes firmware and/or software installed thereon that controls a functionality of scanner 150. The processing device of controller module 225 may be or include a microcontroller, a DSP, a PLC, a microprocessor or programmable logic device such as an FPGA or a CPLD. The processing device may additionally or alternatively include one or more special purpose processor and/or general purpose processor, such as a complex instruction set computing (CISC) microprocessor, reduced instruction set computing (RISC) microprocessor, very long instruction word (VLIW) microprocessor, processor implementing other instruction sets, or processor implementing a combination of instruction sets. Examples of special-purpose processing devices include an application specific integrated circuit (ASIC), a field programmable gate array (FPGA), a digital signal processor (DSP), and network processor.

The memory of controller module 225 may include a non-volatile memory (e.g., RAM) and/or a volatile memory (e.g., ROM, Flash, etc.).

As shown, scanner 150 wirelessly connects to computing device 105 via a wireless connection 207. Scanner 150 may exchange data with computing device 1512 via the wireless connection 207. Scanner 150 is not physically connected (e.g., via a cable) to any computing device or power supply. Accordingly, scanner 150 operates in a fully wireless mode of operation, and draws on power from onboard batteries of battery module 222 and/or on backup power source 272, and exchanges data with computing device 105 via wireless connection 207.

In embodiments, computing device 105 is a component of a scanner cart 290. Scanner cart 290 may include an onboard medical grade power adapter (not shown), and may include a charger 292 for charging scanner 150 and/or a battery pack (e.g., housing one or more replaceable batteries) that can be removed from scanner 150. Cart 290 may further include an onboard cradle for holding the scanner 150 when scanner 150 is not in use. In some embodiments, charger 292 is also a cradle for scanner 150.

In embodiments, controller module 225 detects when a replaceable battery (e.g., a replaceable battery pack) has been removed from scanner 150. Controller module 225 may detect removal of the battery via a battery presence detector, such as a button or sensor. Alternatively, or additionally, controller module 225 may detect a loss of power, and may determine that the battery has been removed based on the loss of power.

Responsive to detecting removal of the replaceable battery, controller module 225 may cause scanner 150 to enter a low power mode. This may include deactivating or shutting down certain components, such as the light projectors 202, cameras 204, IMU 206 and/or temperature control device 208, for example. Additionally, while in the low power mode controller module 225 may shut down a programmable logic (e.g., FPGA) power of an onboard processing device of the controller module 225. In one embodiment, while in the low power mode all functions of the intraoral scanner 150 are powered off except for onboard memory (e.g., DDR) and wireless communication module 215 (e.g., a peripheral component interconnect express (PCIe) connection to wireless communication module 215). This enables scanner 150 to continue to maintain stored state and data in memory and to continue to communicate with computing device 105 during the low power mode. In some embodiments, scanner 150 includes a screen (e.g., a touchscreen), which may or may not be deactivated during the low power mode. While in the low power mode, power consumption of scanner 150 may be minimized. This increases the amount of time that a user has to insert a new replaceable battery into the battery module 222 before the backup power source 272 runs out of power. In one embodiment, power consumption of the scanner 150 is less than about 1.2 W (e.g., less than 1.2 W, less than 1 W, etc.) during the low power mode.

In embodiments, a spare replaceable battery may be stored on cart 290 (e.g., in charger 292). When the replaceable battery is removed from scanner 150, the spare replaceable battery may be removed from charger 292 and inserted into scanner 150, and the replaceable battery that was removed from scanner 150 may be inserted into charger 292. This sequence may be performed in less than 45 seconds or less than 30 seconds in embodiments.

Figure 3A:
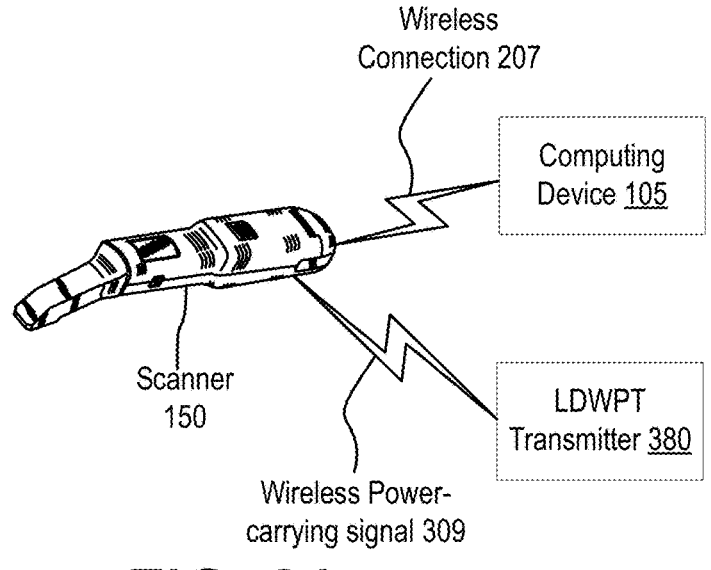
FIGS. 3A-B illustrate an intraoral scanner with a long distance wireless power transfer (LDWPT) receiver wirelessly connected to a computing device via a wireless connection, in accordance with embodiments of the present disclosure.
Figure 3B:
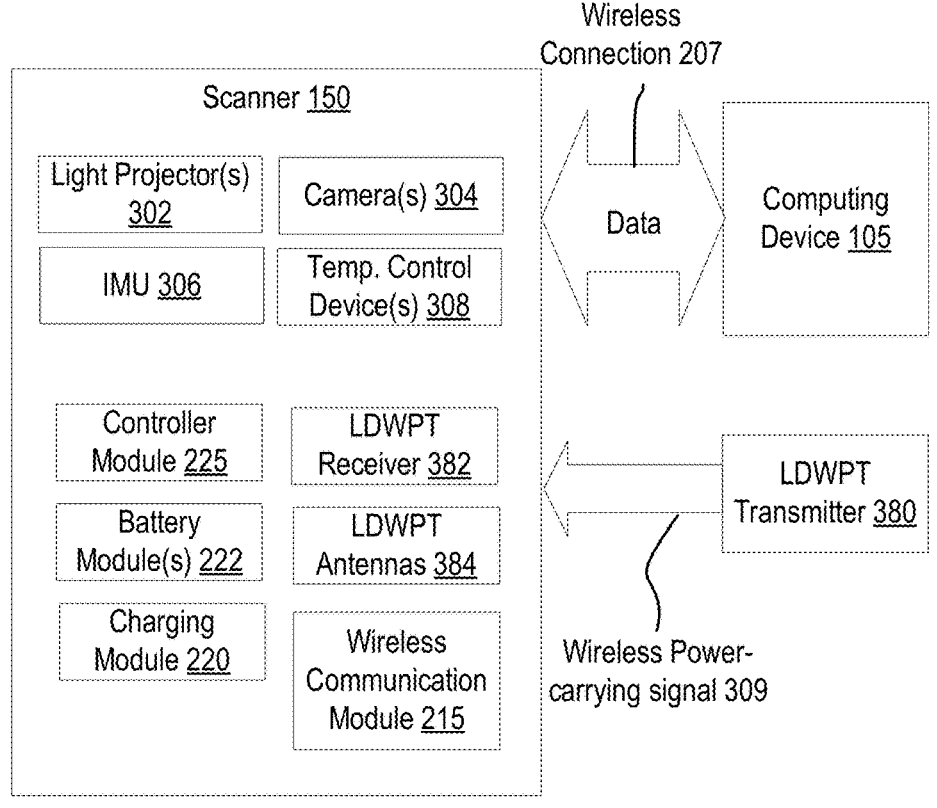

FIGS. 3A-B illustrate an intraoral scanner 150 that includes a long distance wireless power transfer (LDWPT) receiver 382 wirelessly connected to a computing device 105 via a wireless connection 207, in accordance with embodiments of the present disclosure. Scanner 150 may include many of the components discussed with reference to FIGS. 2A-B, such as one or more light projectors 302, one or more cameras 304, an IMU 306 (or other devices for measuring acceleration, rotation, and so on), one or more temperature control devices 308, a controller module 225, one or more battery modules 222, a charging module 220, a wireless communication module 215, and so on. Scanner 150 may exchange data with computing device 105 via wireless connection 207.

In embodiments, scanner 150 includes an LDWPT receiver 382 connected to one or more LDWPT antennas 384. The LDWPT antennas 384 are configured to receive a wireless power-carrying signal 309 from an LDWPT transmitter 380. The LDWPT transmitter 380 may be a component of computing device 105 or may be a separate device from the computing device 105 in embodiments. In one embodiment, the LDWPT transmitter 380 is a component of a scanner cart, such as the scanner cart shown in FIG. 2A. In one embodiment, the LDWPT transmitter 380 is disposed in a ceiling of a dental office. In one embodiment, the wireless power-carrying has a frequency of about 2.4 GHz. In one embodiment, the wireless power-carrying signal has a frequency of about 5 GHz. In one embodiment, the wireless power-carrying signal has a frequency of about 24 GHz. For embodiments using the wireless power-carrying signal with a frequency of about 24 GHz, the LDWPT antennas can have a reduced size as to the size of antennas for receiving wireless power-carrying signals at lower frequencies. In one embodiment, the LDWPT receiver 382 has a dimension of about 1.2×1.2 cm. In one embodiment, the LDWPT receiver 382 has a dimension of about 10×10 cm or smaller.

In embodiments, the LDWPT transmitter 380 is positioned about 60 cm or less away from the scanner 150.

In one embodiment, the scanner 150 includes a body and a probe at a first end of the body. The wireless communication module 215, cameras 304 (e.g., one or more optical sensors configured to receive light that enters the scanner and to generate intraoral scan data based on the received light), and power source (e.g., battery module(s) 222) may be housed within the body. The LDWPT receiver 382 and LDWPT antennas 384 may also be housed within the body. In one embodiment, the LDWPT antennas 384 are disposed within the body at a second end of the body that is opposite the first end that includes the probe.

Figure 4A:
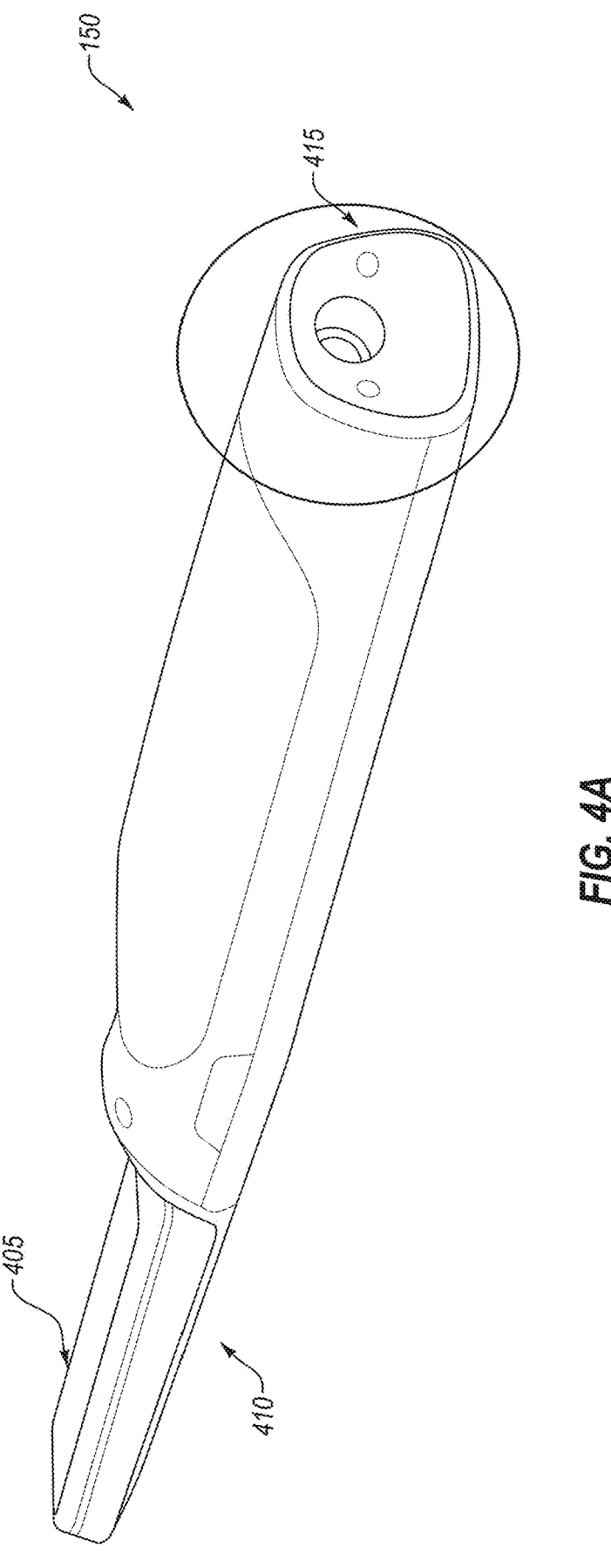
FIG. 4A illustrates an intraoral scanner with an LDWPT receiver, in accordance with embodiments of the present disclosure.

FIG. 4A illustrates an intraoral scanner 150 with a probe 405 at a first end and an LDWPT receiver and LDWPT antennas 415 disposed at a second end, in accordance with embodiments of the present disclosure.

Referring back to FIGS. 3A-B, In one embodiment, the LDWPT antennas 384 are arranged in an array, where each antenna in the array may have a different orientation from other antennas in the array.

Figures 4B, 4C:
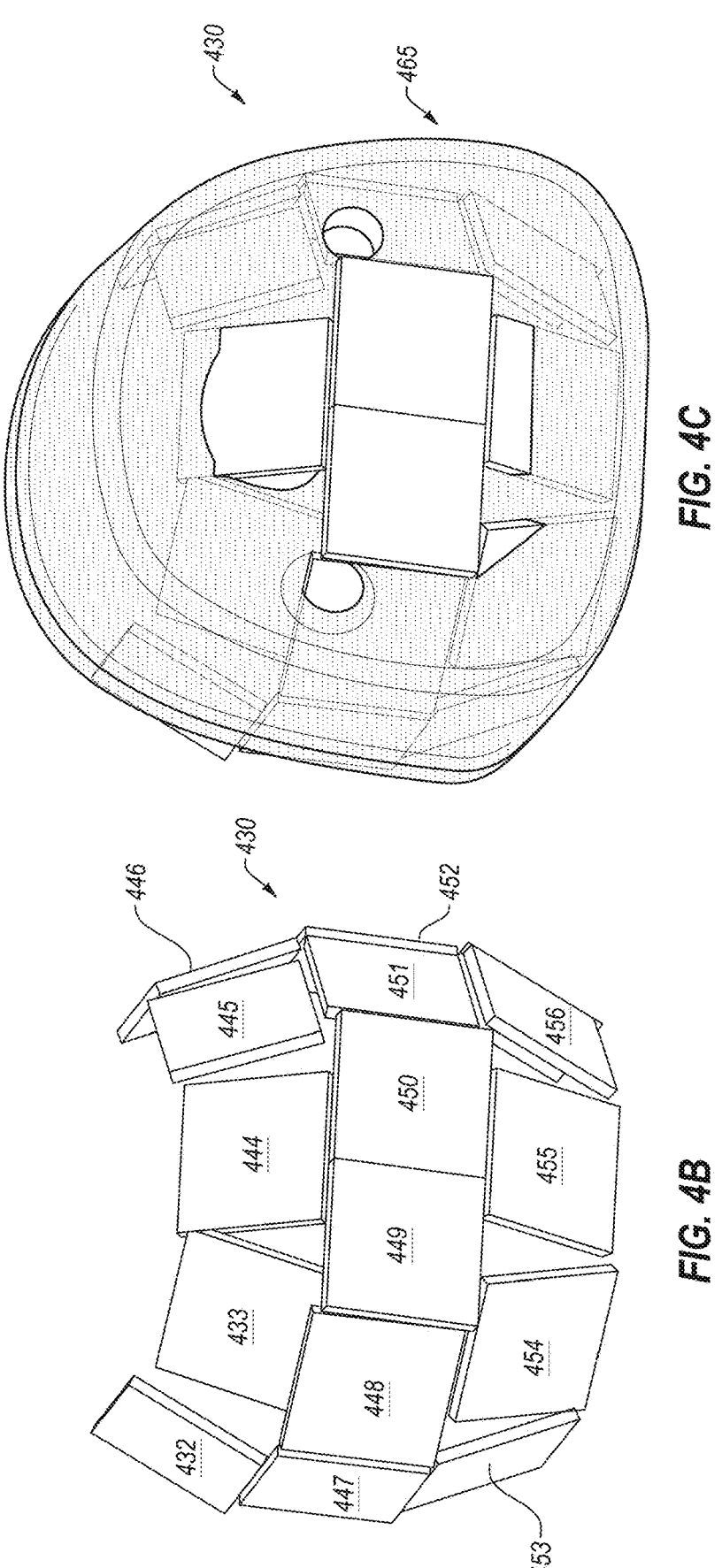
FIG. 4B illustrates an antenna array for an LDWPT receiver used in an intraoral scanner, in accordance with embodiments of the present disclosure.
FIG. 4C illustrates the antenna array for an LDWPT receiver of FIG. 4B together with a power envelope, in accordance with embodiments of the present disclosure.

FIG. 4B illustrates an antenna array 430 for an LDWPT receiver used in an intraoral scanner, in accordance with embodiments of the present disclosure. The antenna array 403 includes LDWPT antennas 432-456. More or fewer LDWPT antennas than those shown may be used in embodiments. As shown, different antennas may have different orientations, though some antennas may share the same orientation. By arranging the antennas in an array, where many antennas have different orientations, the chance that at least one antenna faces towards the LDWPT transmitter and has an uninterrupted line of sight to the LDWPT transmitter is increased.

FIG. 4C illustrates the antenna array 430 for an LDWPT receiver of FIG. 4B together with a power envelope 465 that shows the angles from which the antenna array scan receive power from a wireless power-carrying signal, in accordance with embodiments of the present disclosure.

Figure 4D:
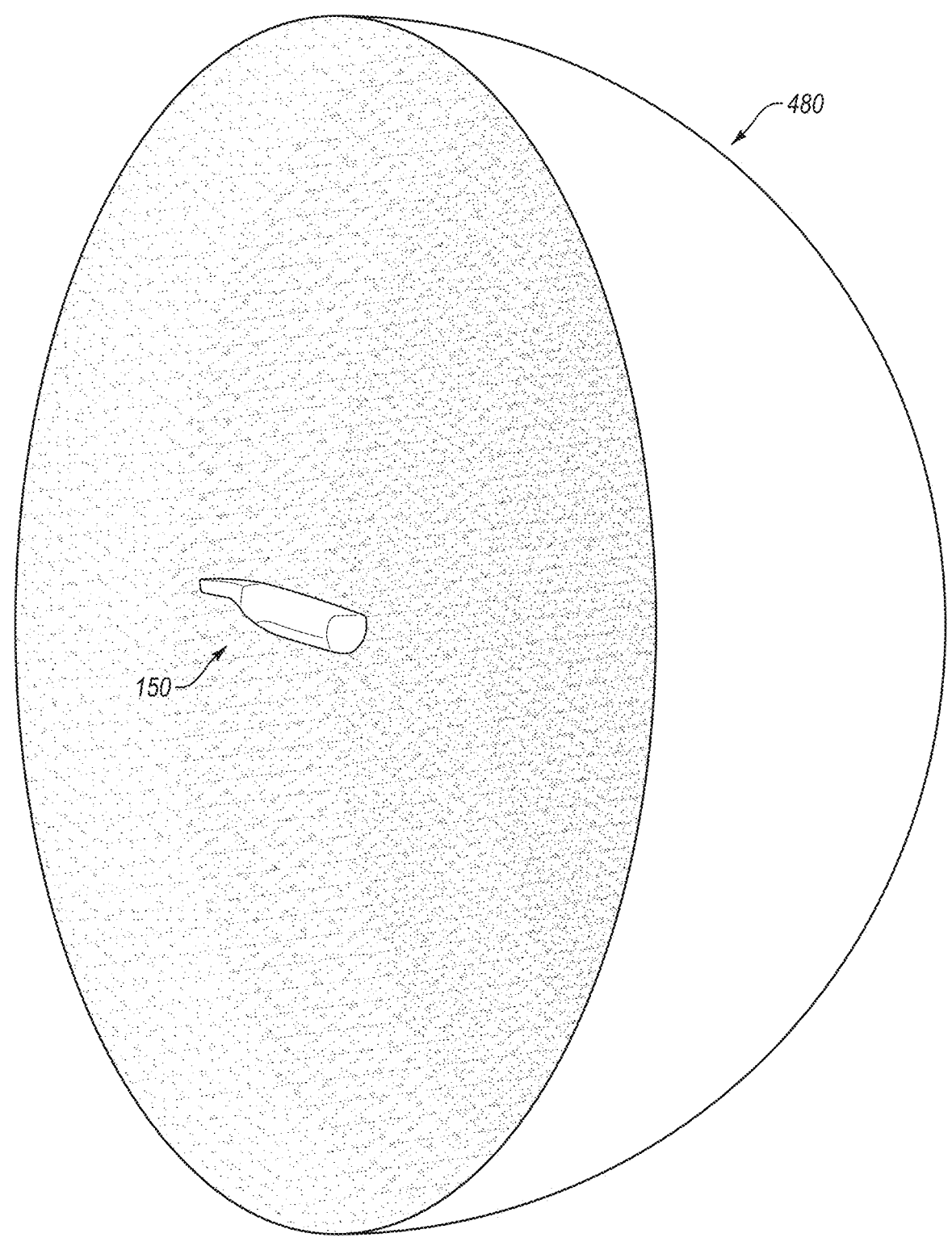
FIG. 4D illustrates the intraoral scanner of FIG. 4A inside of a power distribution hemisphere, in accordance with embodiments of the present disclosure.

FIG. 4D illustrates the intraoral scanner 150 of FIG. 4A inside of a power distribution hemisphere 480, in accordance with embodiments of the present disclosure. In the illustrated example, the power distribution hemisphere 480 has a radius of 60 cm, where the antenna array of the intraoral scanner 150 is at the center of the radius. The power distribution hemisphere can be used to model power distribution to the intraoral scanner and to analyze the minimum wireless power that can be produced by antennas at a given distance between the antennas and the LDWPT transmitter (e.g., distance of 60 cm). The energy that will be received by a given antenna is dependent on the angle between a surface of the LDWPT transmitter and a normal of the antenna. The power distribution hemisphere 480 was triangulated, and for every vertex on the hemisphere a sum of energy from all of the antennas of the antenna array of the scanner 150 were calculated.

Figure 5:
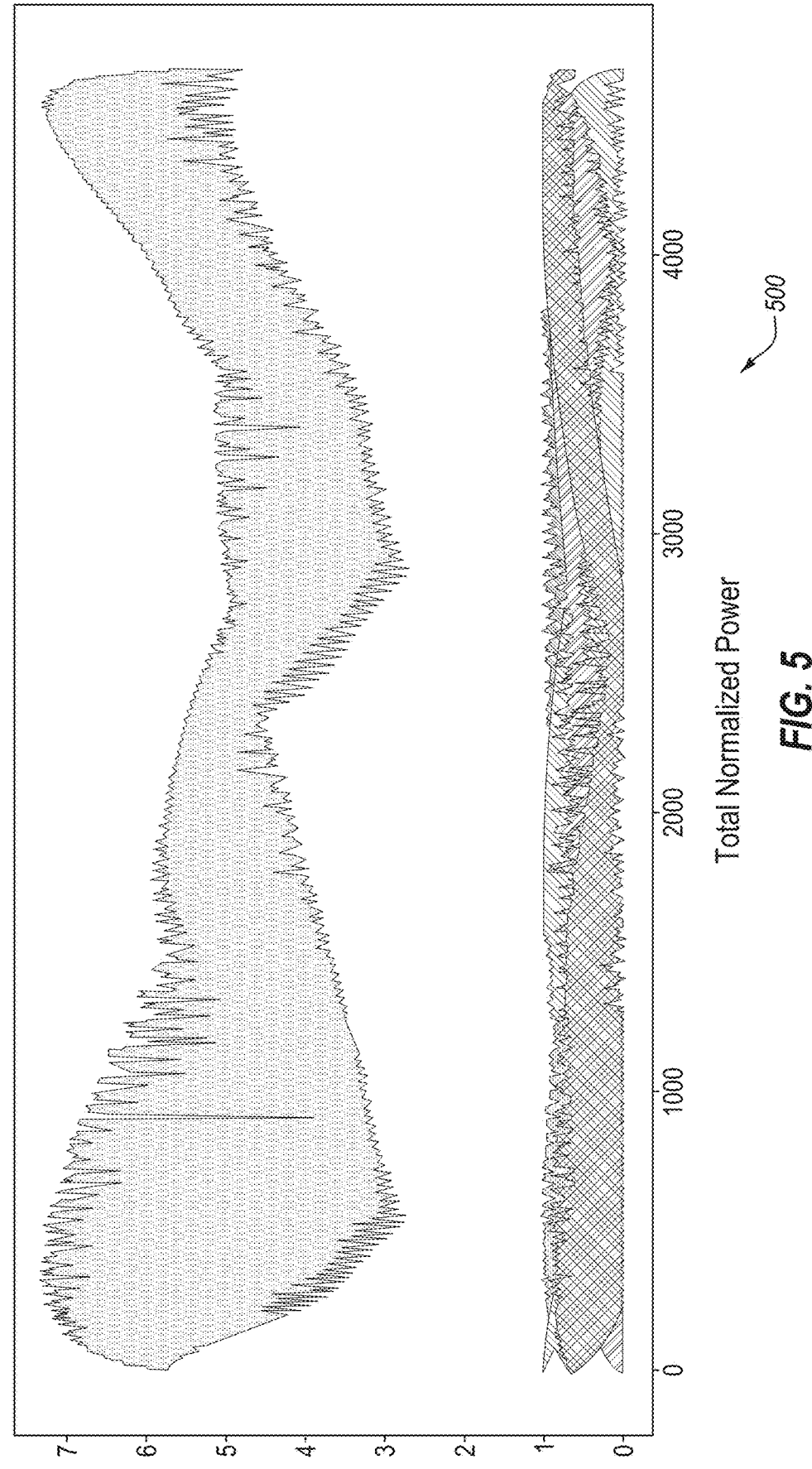
FIG. 5 illustrates total normalized power for the intraoral scanner of FIG. 4A, in accordance with embodiments of the present disclosure.

FIG. 5 illustrates total normalized power for the intraoral scanner of FIG. 4A based on the power distribution hemisphere of FIG. 4D, in accordance with embodiments of the present disclosure. As shown in FIG. 5, total power (top) is in the range of 3-7.5, while the power for single receivers (bottom) is between 0 and 1. Using a worst case scenario, the total normalized power is 3, which is 1.02 W. To increase the power delivered to the intraoral scanner, a size of the LDWPT transmitter can be increased (e.g., to a 15×15 cm transmitter), which can produce 5.49 W of total power in embodiments. In embodiments, the LDWPT receiver can receive about 4-6 W of wireless power from the LDWPT transmitter at any given time.

Returning to FIGS. 3A-B, in embodiments the battery module 222 includes a rechargeable battery having a rating of 500-600 mAh, as opposed to the rating of 2000-3500 mAh used for the batteries of other wireless intraoral scanners. Such a reduction in the battery size can significantly reduce a weight of the scanner 150. For example, the battery may have a weight of about 10 grams as opposed to a weight of about 65 grams for batteries in traditional wireless intraoral scanners. The smaller battery can provide backup power to power the scanner 150 while the wireless power-carrying signal 309 is interrupted.

Figure 7A:
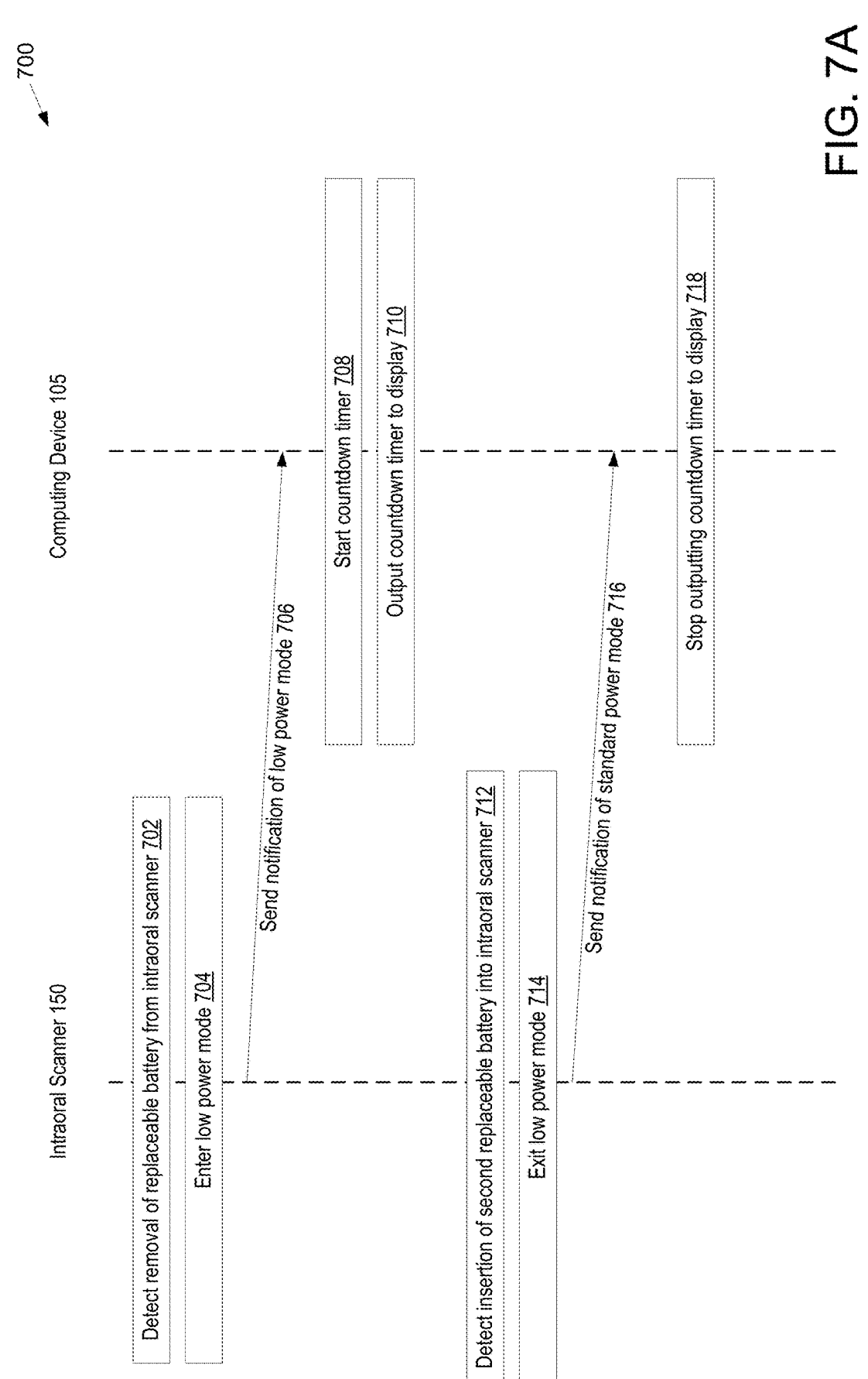
FIG. 7A is a sequence diagram illustrating an exchange between an intraoral scanner and a computing device during a battery replacement process, in accordance with embodiments of the present disclosure.
Figure 7B:
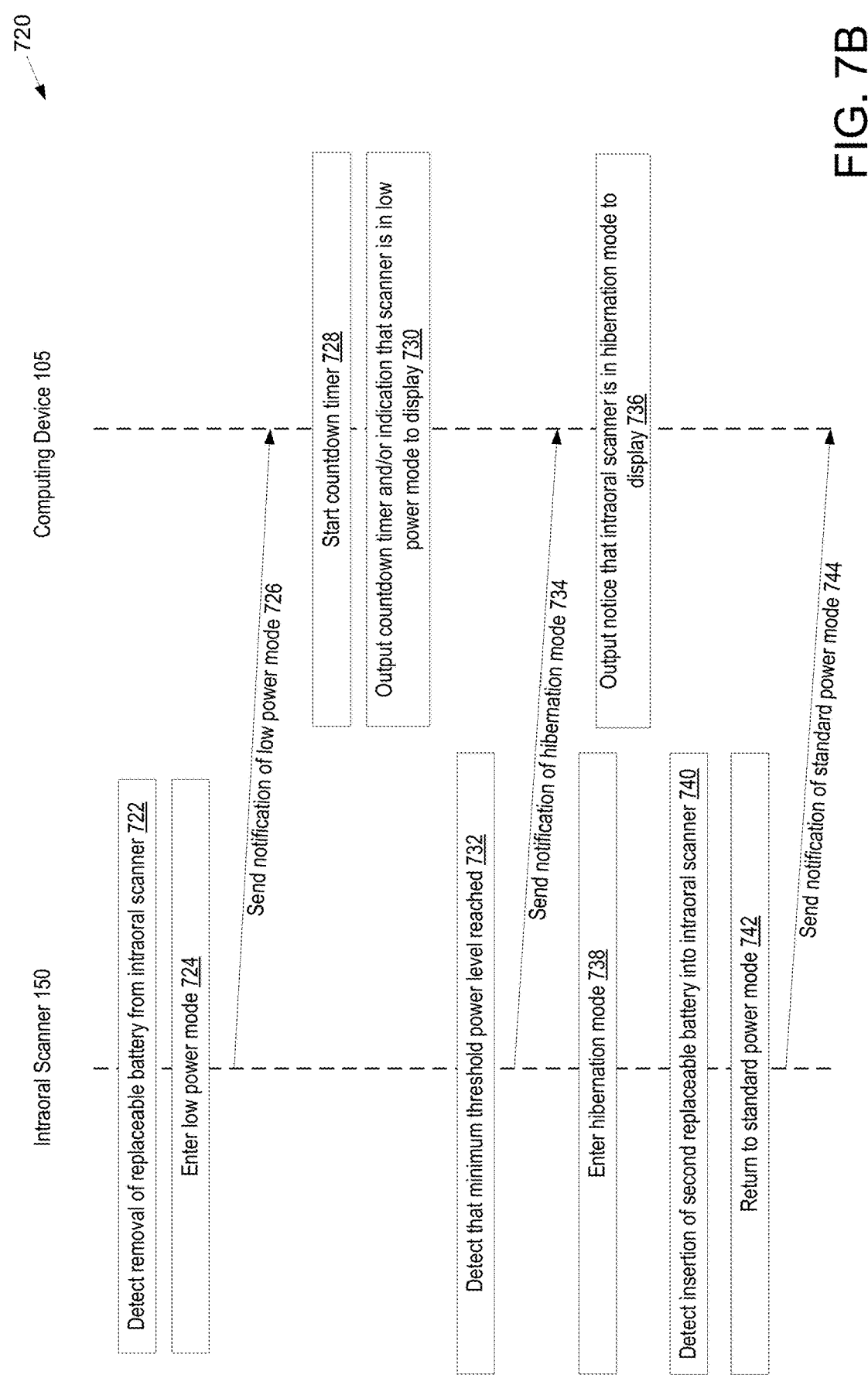
FIG. 7B is a sequence diagram illustrating an exchange between an intraoral scanner and a computing device with regards to a power state of the intraoral scanner, in accordance with embodiments of the present disclosure.
Figure 7C:
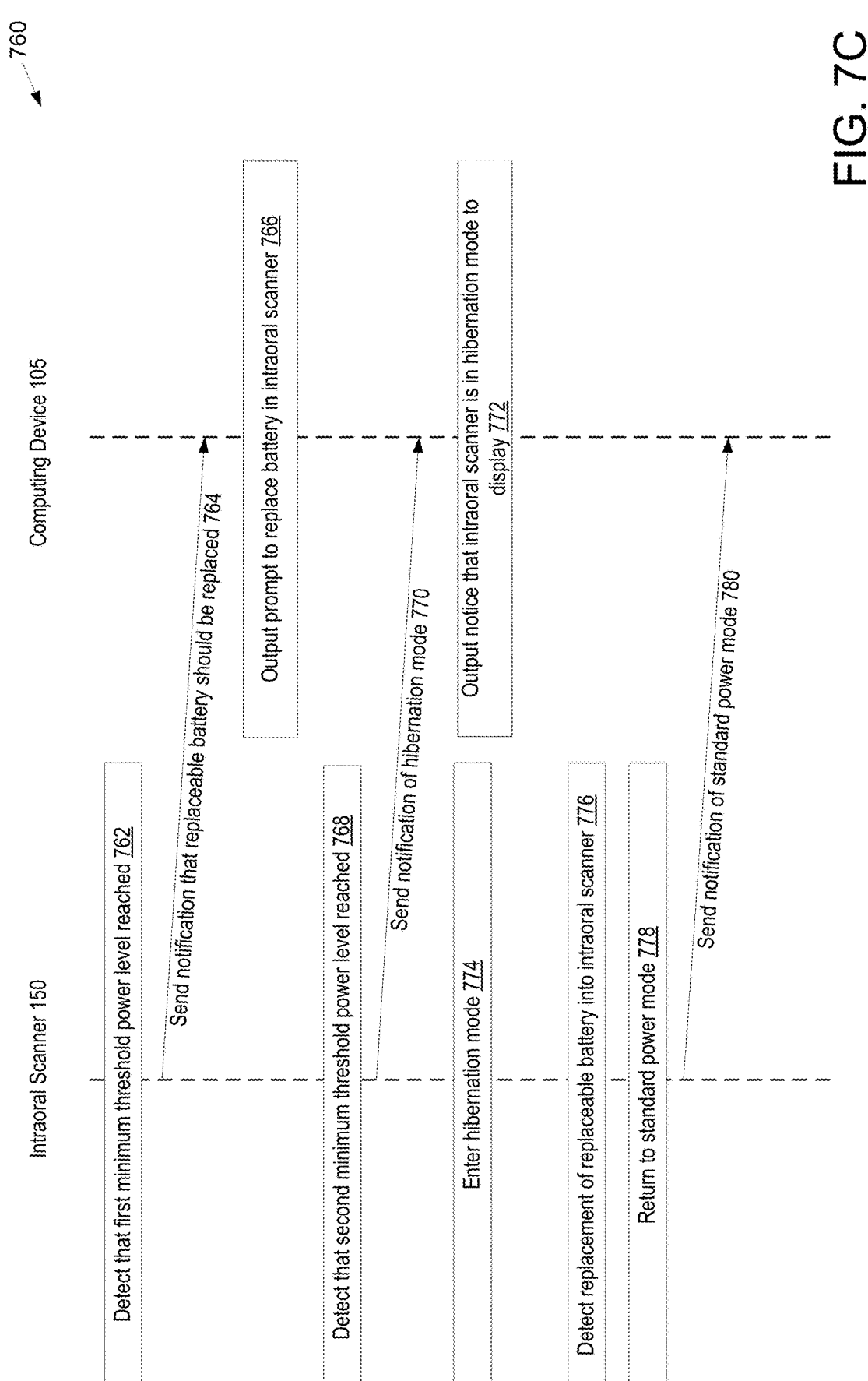
FIG. 7C is a sequence diagram illustrating another exchange between an intraoral scanner and a computing device with regards to a power state of the intraoral scanner, in accordance with embodiments of the present disclosure.

FIGS. 6-7C illustrate methods related to power management of a wireless intraoral scanner, according to embodiments. Operations of the methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by an intraoral scanning system that includes an intraoral scanner and a computing device wirelessly connected to the intraoral scanner.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

FIG. 6 illustrates a flow diagram for a method 600 of power conservation for an intraoral scanner, in accordance with embodiments of the present disclosure. At block 606 of method 600, processing logic of an intraoral scanner detects removal of a replaceable battery from the intraoral scanner. At block 608, processing logic transitions the intraoral scanner from a standard power mode to a low power mode. This may include, at block 610, deactivating light projectors, cameras, an IMU, temperature control devices and/or a programmable logic portion of a processing device.

In one embodiment, at block 612 processing logic notifies a computing device to which the intraoral scanner is wirelessly connected that the scanner has entered or is about to enter the lower power mode.

In one embodiment, at block 616 processing logic starts a timer. The timer may be calibrated so that the timer will count down to zero when a backup power source of the intraoral scanner will run out of power, causing the intraoral scanner to turn off. In one embodiment, at block 618 processing logic determiner a remaining time of the timer and outputs an indicator of the remaining time. The indicator may include, for example, a solid or flashing light on the intraoral scanner. The shade or color of the light may change and/or a frequency of pulsing or flashing of the light may change as the remaining time of the timer decreases to notify a user of the amount of time that they have remaining. In one embodiment, the intraoral scanner includes a display (e.g., a touchscreen), and a status of the timer is output to the display (e.g., via an analog or digital indication of an amount of remaining time).

Figure 8:
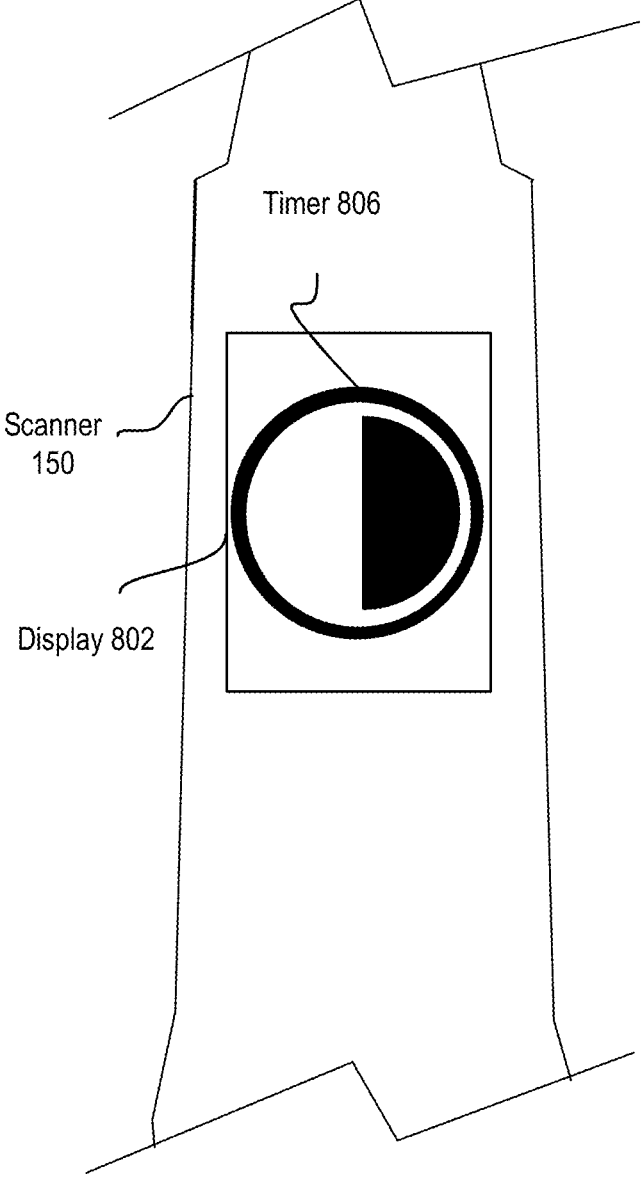
FIG. 8 illustrates a display on an intraoral scanner during a low power mode, in accordance with embodiments of the present disclosure.

FIG. 8 illustrates a display 802 on an intraoral scanner 150 during a low power mode, in accordance with embodiments of the present disclosure. As shown the display 802 may show a current state of a timer 806 indicating an amount of time remaining before the scanner runs out of power.

Returning to FIG. 6, in one embodiment at block 618 processing logic determines a remaining charge in a backup power source. Processing logic may then output the remaining power to a display of the intraoral scanner, such as the display shown in FIG. 8.

In one embodiment, at block 619 processing logic notifies the computing device of the remaining time and/or the remaining charge. The computing device may then output the remaining time and/or remaining charge to a display of the computing device.

At block 626, processing logic may determine whether a remaining time and/or a remaining charge are below a threshold. If the remaining time is below a remaining time threshold or the remaining charge is below a minimum charge threshold, the method may continue to block 626. Otherwise the method may proceed to block 646.

At block 630, processing logic may notify the computing device of an impending hibernation mode (e.g., that the intraoral scanner is about to enter the hibernation mode). At block 636, processing logic transitions the intraoral scanner to the hibernation mode from the low power mode. This may include at block 640 shutting down additional components of the intraoral scanner, such as a wireless communication module, a remainder of a processing device, and so on. In one embodiment, every component of the intraoral scanner other than memory (and optionally a battery detector) are powered down or deactivated for the hibernation mode. The hibernation mode may maintain a state of the intraoral scanner and any data in memory (e.g., a volatile memory) of the intraoral scanner. The method may then continue to block 646.

At block 646, processing logic determines whether a replacement battery is detected (e.g., whether a new replacement battery have been inserted into the intraoral scanner). If no replacement battery is detected, the method may return to block 626 if the intraoral scanner is in the low power mode or may return to block 646 if the intraoral scanner is in the hibernation mode. If at block 646 a replacement batter is detected, the method proceeds to block 660. At block 660, processing logic transitions the intraoral scanner out of either the low power mode or the hibernation mode. This may include turning on or reactivating some or all of the deactivated components of the intraoral scanner. In one embodiment, this may include booting up an operating system and reestablishing a wireless connection with the computing device if the intraoral scanner had entered the hibernation mode. This may also include reheating the intraoral scanner to reach a target temperature, turning on cameras, an IMU, light projectors, programmable logic, and so on. Once the intraoral scanner is returned to the standard power mode, it may commence performing an intraoral scan.

FIG. 7A is a sequence diagram 700 illustrating an exchange between an intraoral scanner 150 and a computing device 105 during a battery replacement process, in accordance with embodiments of the present disclosure. In one embodiment, at block 702 the intraoral scanner detects removal of a replaceable battery from the intraoral scanner. At block 704, the intraoral scanner enters a low power mode. At block 706, the intraoral scanner sends a notification of the low power mode to the computing device. At block 708, the computing device may start a countdown timer. The computing device may be configured such that the countdown timer will time out when a backup power source of the intraoral scanner runs out of power. At block 710, the computing device may output the countdown timer to a display. The computing device may also output an audio indication of the countdown timer (e.g., a verbal countdown).

At block 712, the intraoral scanner detects insertion of a second replaceable battery into the intraoral scanner. At block 714, the intraoral scanner exits the lower power mode. At block 716, the intraoral scanner sends a notification that the intraoral scanner has resumed a standard power mode to the computing device. At block 718, the computing device stops the countdown timer and stops outputting the countdown timer to a display.

FIG. 7B is a sequence diagram 720 illustrating an exchange between an intraoral scanner 150 and a computing device 105 with regards to a power state of the intraoral scanner, in accordance with embodiments of the present disclosure. In one embodiment, at block 722 the intraoral scanner detects removal of a replaceable battery from the intraoral scanner. At block 724, the intraoral scanner enters a low power mode. At block 726, the intraoral scanner sends a notification of the low power mode to the computing device. At block 728, the computing device may start a countdown timer. At block 730, the computing device may output the countdown timer to a display. The computing device may also output an audio indication of the countdown timer (e.g., a verbal countdown).

At block 732, the intraoral scanner detects that a minimum threshold power level has been reached (e.g., that a backup power source has discharged power such that it reaches the minimum threshold power level). At block 734, the intraoral scanner sends a notification that the intraoral scanner is entering a hibernation mode to the computing device. At block 736, the computing device outputs a notice that the intraoral scanner is in the hibernation mode to a display. At block 738, the intraoral scanner enters the hibernation mode.

At block 740, the intraoral scanner detects insertion of a second replaceable battery into the intraoral scanner. At block 742, the intraoral scanner returns to a standard power mode (e.g., exits the hibernation mode). At block 744, the intraoral scanner sends a notification that the intraoral scanner has resumed the standard power mode to the computing device. The computing device may then stop outputting the notice that the intraoral scanner is in the hibernation mode.

FIG. 7C is a sequence diagram 760 illustrating another exchange between an intraoral scanner 150 and a computing device 105 with regards to a power state of the intraoral scanner 150, in accordance with embodiments of the present disclosure. At block 762, the intraoral scanner detects that a first minimum threshold power level has been reached. The first minimum threshold power level may be, for example 1-10% of a total power storage level of a replaceable battery of the intraoral scanner. At block 764, the intraoral scanner sends a notification that the replaceable battery should be replaced to the computing device. At block 766, the computing device outputs a prompt for a user to replace the replaceable battery of the intraoral scanner to a display. In one embodiment, a user may respond to the prompt by selecting an option that they do not have a backup battery to use. This may cause the intraoral scanner to use up the power of the backup power source before entering a hibernation mode (e.g., may adjust a second minimum threshold power level used to determine when to enter a hibernation mode).

At block 768, the intraoral scanner detects that a second minimum threshold power level is reached. The second minimum threshold power level may be lower than the first minimum threshold power level. The second minimum threshold power level may be, for example 1-5% of a total power storage level of the replaceable battery of the intraoral scanner.

At block 770, the intraoral scanner may send a notification that the intraoral scanner is about to enter a hibernation mode to the computing device. At block 772, the computing device may output a notice that the intraoral scanner is in the hibernation mode to a display.

At block 774, the intraoral scanner enters the hibernation mode. In one embodiment, intraoral scanner 150 determines whether it is currently in use prior to entering the hibernation mode. If the intraoral scanner is currently in use, then the intraoral scanner may not enter the hibernation mode. In one embodiment, a user may configure the intraoral scanner to enter hibernation mode or not to enter hibernation mode under such circumstances.

At block 776, the intraoral scanner detects replacement of the replaceable battery of the intraoral scanner. At block 778, the intraoral scanner returns to a standard power mode. At block 780, the intraoral scanner may send a notification of standard power mode to computing device 105. In one embodiment, after returning to the standard power mode the intraoral scanner reestablishes a wireless connection to the computing device, which inherently notifies the computing device that the intraoral scanner has returned to the standard power mode.

Figure 9:
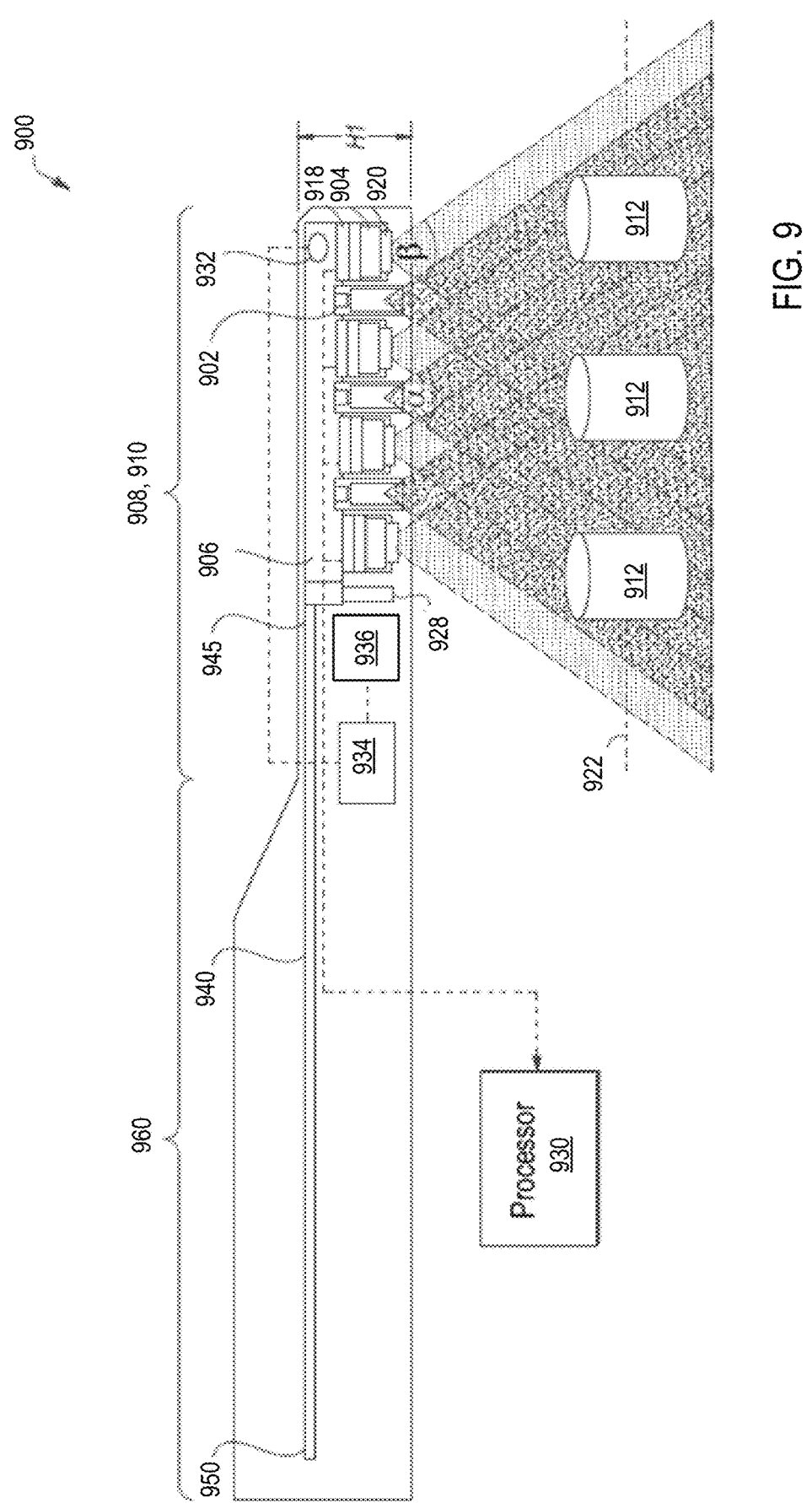
FIG. 9 illustrates an example intraoral scanner, in accordance with embodiments of the present disclosure.

Reference is now made to FIG. 9, which is a schematic illustration of an intraoral scanner 900 comprising an elongate handheld wand (e.g., a body with a probe at one end of the body), in accordance with some applications of the present disclosure. The intraoral scanner 900 may include a wireless module (not shown), replaceable battery, an LDWPT receiver and/or other components discussed herein disposed in a body of the intraoral scanner 900. The intraoral scanner 900 may correspond to intraoral scanner 150 of FIGS. 1-3B in embodiments. Intraoral scanner 900 includes a plurality of structured light projectors 902 and a plurality of cameras 904 that are coupled to a rigid structure 906 disposed within a probe 908 at a distal end 910 of the body of the intraoral scanner 900. In some applications, during an intraoral scanning procedure, probe 908 is inserted into the oral cavity of a subject or patient.

For some applications, structured light projectors 902 are positioned within probe 908 such that each structured light projector 902 faces an object 912 outside of intraoral scanner 900 that is placed in its field of illumination, as opposed to positioning the structured light projectors in a proximal end of the handheld wand and illuminating the object by reflection of light off a mirror and subsequently onto the object. Alternatively, the structured light projectors may be disposed at a proximal end of the handheld wand. Similarly, for some applications, cameras 904 and/or other optical sensors are positioned within probe 908 such that each camera 904 faces an object 912 outside of intraoral scanner 900 that is placed in its field of view, as opposed to positioning the cameras in a proximal end of the intraoral scanner and viewing the object by reflection of light off a mirror and into the camera. This positioning of the projectors and the cameras within probe 908 enables the scanner to have an overall large field of view while maintaining a low profile probe. Alternatively, the cameras may be disposed in a proximal end of the handheld wand.

In some applications, cameras 904 each have a large field of view β (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In one embodiment, a field of view (beta) for each camera is between 80 and 90 degrees, which may be particularly useful because it provided a good balance among pixel size, field of view and camera overlap, optical quality, and cost. Cameras 904 may include an image sensor 918 and objective optics 920 including one or more lenses. To enable close focus imaging, cameras 904 may focus at an object focal plane 922 that is located between 1 mm and 30 mm, e.g., between 4 mm and 24 mm, e.g., between 5 mm and 11 mm, e.g., 9 mm-10 mm, from the lens that is farthest from the sensor. In some applications, cameras 904 may capture images at a frame rate of at least 30 frames per second, e.g., at a frame of at least 75 frames per second, e.g., at least 100 frames per second. In some applications, the frame rate may be less than 200 frames per second.

A large field of view achieved by combining the respective fields of view of all the cameras may improve accuracy due to reduced amount of image stitching errors, especially in edentulous regions, where the gum surface is smooth and there may be fewer clear high resolution 3D features. Having a larger field of view enables large smooth features, such as the overall curve of the tooth, to appear in each image frame, which improves the accuracy of stitching respective surfaces obtained from multiple such image frames.

Similarly, structured light projectors 902 may each have a large field of illumination a (alpha) of at least 45 degrees, e.g., at least 70 degrees. In some applications, field of illumination a (alpha) may be less than 120 degrees, e.g., than 100 degrees.

For some applications, in order to improve image capture, each camera 904 has a plurality of discrete preset focus positions, in each focus position the camera focusing at a respective object focal plane 922. Each of cameras 904 may include an autofocus actuator that selects a focus position from the discrete preset focus positions in order to improve a given image capture. Additionally or alternatively, each camera 904 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the sensor.

In some applications, structured light projectors 902 and cameras 904 are coupled to rigid structure 906 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 922 that is located at least 4 mm from the lens that is farthest from the sensor. Due to different possible configurations of the projectors and cameras, some of the projected pattern may never be seen in the field of view of any of the cameras, and some of the projected pattern may be blocked from view by object 912 as the scanner is moved around during a scan.

Rigid structure 906 may be a non-flexible structure to which structured light projectors 902 and cameras 904 are coupled so as to provide structural stability to the optics within probe 908. Coupling all the projectors and all the cameras to a common rigid structure helps maintain geometric integrity of the optics of each structured light projector 902 and each camera 904 under varying ambient conditions, e.g., under mechanical stress as may be induced by the subject's mouth. Additionally, rigid structure 906 helps maintain stable structural integrity and positioning of structured light projectors 902 and cameras 904 with respect to each other.

For some applications, there is at least one uniform light projector 928 (which may be an unstructured light projector that projects light across a range of wavelengths) coupled to rigid structure 906. Uniform light projector 928 may transmit white light onto object 912 being scanned. At least one camera, e.g., one of cameras 904, captures two-dimensional color images of object 912 using illumination from uniform light projector 928. Light reflecting off of the object 912 may enter the scanner head and be received by the cameras. The cameras may then generate intraoral scan data based on the received light. The wireless communication module may wirelessly send the intraoral scan data to a computing device in embodiments.

A processor or processing device 930 of the computing device may run a surface reconstruction algorithm that may use detected patterns (e.g., dot patterns) projected onto object 912 to generate a 3D surface of the object 912. In some embodiments, the processor 930 may combine at least one 3D scan captured using illumination from structured light projectors 902 with a plurality of intraoral 2D images captured using illumination from uniform light projector 928 in order to generate a digital three-dimensional image of the intraoral three-dimensional surface. Using a combination of structured light and uniform illumination enhances the overall capture of the intraoral scanner and may help reduce the number of options that processor 930 needs to consider when running a correspondence algorithm used to detect depth values for object 912. In one embodiment, the intraoral scanner and correspondence algorithm described in U.S. application Ser. No. 16/446,181, filed Jun. 19, 2019, is used. U.S. application Ser. No. 16/446,181, filed Jun. 19, 2019, is incorporated by reference herein in its entirety. In embodiments, processor 930 may be a processor of computing device 105 of FIG. 1. Alternatively, processor 930 may be a processor integrated into the intraoral scanner 900.

For some applications, all data points taken at a specific time are used as a rigid point cloud, and multiple such point clouds are captured at a frame rate of over 10 captures per second. The plurality of point clouds are then stitched together using a registration algorithm, e.g., iterative closest point (ICP), to create a dense point cloud. A surface reconstruction algorithm may then be used to generate a representation of the surface of object 912.

For some applications, at least one temperature sensor 932 is coupled to rigid structure 906 and measures a temperature of rigid structure 906. Temperature control circuitry

934 disposed within intraoral scanner 900 (a) receives data from temperature sensor 932 indicative of the temperature of rigid structure 906 and (b) activates a temperature control unit 936 in response to the received data. Temperature control unit 936, e.g., a PID controller, keeps probe 908 at a target temperature (e.g., between 35 and 43 degrees Celsius, between 37 and 41 degrees Celsius, etc.). Keeping probe 908 above 35 degrees Celsius, e.g., above 37 degrees Celsius, reduces fogging of the glass surface of intraoral scanner 900, through which structured light projectors 902 project and cameras 904 view, as probe 908 enters the oral cavity, which is typically around or above 37 degrees Celsius. Keeping probe 908 below 43 degrees, e.g., below 41 degrees Celsius, prevents discomfort or pain.

In some embodiments, heat may be drawn out of the probe 908 via a heat conducting element 940, e.g., a heat pipe, that is disposed within intraoral scanner 900, such that a distal end 945 of heat conducting element 940 is in contact with rigid structure 906 and a proximal end 950 is in contact with a proximal end 960 of intraoral scanner 900. Heat is thereby transferred from rigid structure 906 to proximal end 960 of intraoral scanner 900. Alternatively or additionally, a fan disposed in a handle region of intraoral scanner 900 may be used to draw heat out of probe 908.

In one embodiment, intraoral scanner 150 corresponds to the intraoral scanner described in U.S. application Ser. No. 16/910,042, filed Jun. 23, 2020 and entitled "Intraoral 3D Scanner Employing Multiple Miniature Cameras and Multiple Miniature Pattern Projectors", which is incorporated by reference herein. In one embodiment, intraoral scanner 150 corresponds to the intraoral scanner described in U.S. application Ser. No. 16/446,181, filed Jun. 19, 2019 and entitled "Intraoral 3D Scanner Employing Multiple Miniature Cameras and Multiple Miniature Pattern Projectors", which is incorporated by reference herein.

In some embodiments, intraoral scanner 900 includes a touchscreen (not shown) disposed on the body of the intraoral scanner 900. The touchscreen may be configured to output a plurality of virtual buttons, to detect a touch input associated with a virtual button of the plurality of virtual buttons, and to provide a signal associated with the touch input of the virtual button to the processor of the computing device. In some embodiments, intraoral scanner 900 may receive an input from the computing device indicating a current mode of an intraoral scan application. Intraoral scanner 900 may then determine the plurality of virtual buttons to output on the touchscreen based on the current mode of the intraoral scan application and/or based on past inputs. Alternatively, the computing device may determine what virtual buttons are to be displayed on the touchscreen, and may provide data on what is to be displayed on the touchscreen to intraoral scanner 900.

In some embodiments an intraoral scanner that performs confocal focusing to determine depth information may be used.

Figure 10:
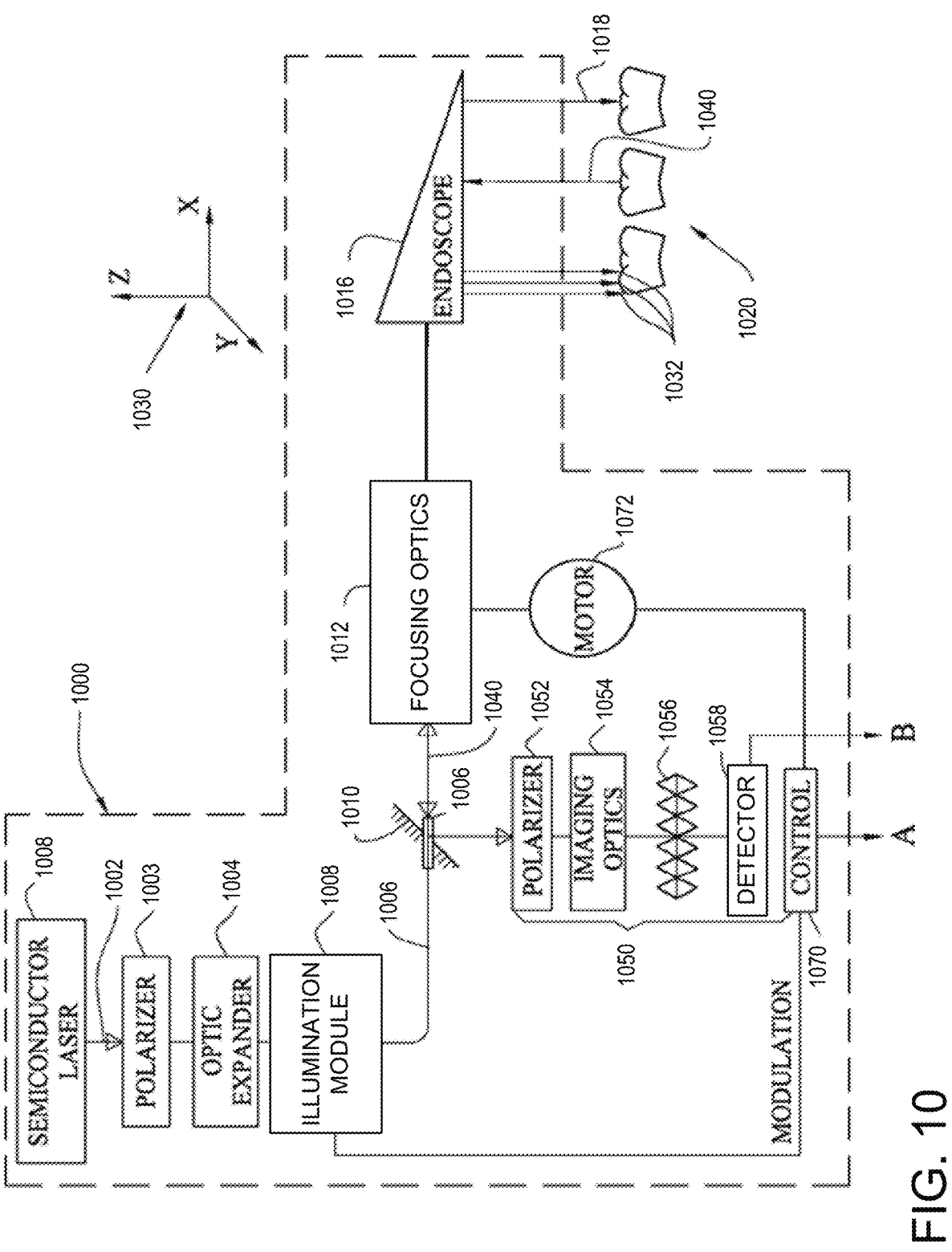
FIG. 10 illustrates another example intraoral scanner, in accordance with embodiments of the present disclosure.

FIG. 10 illustrates a functional block diagram of an intraoral scanner 1000 according to one embodiment. Intraoral scanner 1000 may correspond to intraoral scanner 150 of FIGS. 1-3B in embodiments. Together, the intraoral scanner 1000 and a computing device (e.g., computing device 105) may form a system for generating three dimensional surfaces and/or models of scanned intraoral objects (e.g., an intraoral scanning system). In one embodiment, the intraoral scanner is a confocal intraoral scanner. In one embodiment, intraoral scanner 1000 includes a touchscreen, a wireless communication module, a replaceable battery, an LDWPT receiver, and so on as discussed above.

In one embodiment intraoral scanner 1000 includes a body comprising a probe at one end of the body. The probe includes a scanner head. The probe may include, for example, an endoscope 1016. Intraoral scanner 1000 includes a semiconductor laser unit (illumination module) 1008 in the body that emits focused light (e.g., a focused light beam), as represented by arrow 1002. The light 1002 passes through a polarizer 1003. Polarizer 1003 polarizes the light beam passing through polarizer 1003. Alternatively, polarizer 1003 may be omitted in some embodiments. The light then enters into an optic expander 1004 in the body that improves a numerical aperture of the light 1002. The light 1002 then passes through an illumination module 1008 in the body, which may split the light 1002 into an array of incident light beams 1006, represented here, for ease of illustration, by a single line. The illumination module 1008 may be, for example, a grating or a micro lens array that splits the light 1002 into an array of light beams 1006. In one embodiment, the array of light beams 1006 is an array of telecentric light beams. Alternatively, the array of light beams may not be telecentric.

The intraoral scanner 1000 further includes a unidirectional mirror or beam splitter (e.g., a polarizing beam splitter) 1010 in the body that passes the array of light beams 1006. A unidirectional mirror 1010 allows transfer of light from the semiconductor laser 1008 through to downstream optics, but reflects light travelling in the opposite direction. A polarizing beam splitter allows transfer of light (e.g., light beams) having a particular polarization and reflects light beams having a different (e.g., opposite) polarization. In one embodiment, the unidirectional mirror or beam splitter 1010 has a small central aperture. The small central aperture may improve a measurement accuracy of the intraoral scanner 1000. In one embodiment, as a result of a structure of the unidirectional mirror or beam splitter 1010, the array of light beams will yield a light annulus on an illuminated area of an imaged object as long as the area is not in focus. Moreover, the annulus will become a completely illuminated spot once in focus. This ensures that a difference between measured intensities of out-of-focus points and in-focus points will be larger.

Along an optical path of the array of light beams after the unidirectional mirror or beam splitter 1010 are focusing optics 1012 in the body, and an endoscopic probing member 46 at one end of the body. In one embodiment, the focusing optics are confocal focusing optics. Additionally, a quarter wave plate may be disposed along the optical path after the unidirectional mirror or beam splitter 1010 to introduce a certain polarization to the array of light beams. In some embodiments this may ensure that reflected light beams will not be passed through the unidirectional mirror or beam splitter 1010. Focusing optics 1012 may additionally include relay optics (not shown). Focusing optics 1012 may or may not maintain the same magnification of an image over a wide range of distances in the Z direction, wherein the Z direction is a direction of beam propagation (e.g., the Z direction corresponds to an imaging axis that is aligned with an optical path of the array of light beams 1006). The relay optics enable the intraoral scanner 1000 to maintain a certain numerical aperture for propagation of the array of light beams 1006.

The endoscopic probing member 1016 may include a rigid, light-transmitting medium, which may be a hollow object defining within it a light transmission path or an object made of a light transmitting material, e.g. a glass body or tube. In one embodiment, the endoscopic probing member 1016 include a prism such as a folding prism. At its end, the endoscopic probing member 1016 may include a mirror of the kind ensuring a total internal reflection. Thus, the mirror may direct the array of light beams towards a teeth segment 1020 or other intraoral object. The endoscope probing member 1016 thus emits light 1018 (e.g., an array of light beams), which impinges on to surfaces of the teeth section 1020.

The light 1018 (e.g., array of light beams) may be arranged in an X-Y plane, in the Cartesian frame 1030, propagating along the Z axis. As the surface on which the incident light hits is an uneven surface, illuminated points or locations 1032 are displaced from one another along the Z axis, at different $(X_i, Y_i)$ locations. Thus, while a point at one location may be in focus of the focusing optics 1012, points at other locations may be out-of-focus. Therefore, the light intensity of returned light (e.g., returned light beams) of the focused points will be at its peak, while the light intensity at other points will be off peak. Thus, for each illuminated point, multiple measurements of light intensity are made at different positions along the Z-axis. For each of such $(X_i, Y_i)$ location, the derivative of the intensity over distance (Z) may be made, with the $Z_i$ yielding maximum derivative, $Z_0$, being the in-focus distance. As pointed out above, the incident light from the light 1018 may form a light disk or a blurry image on the surface when out of focus and a complete light spot or a sharp image when in focus. Thus, the distance derivative will be larger when approaching in-focus position, increasing accuracy of the measurement.

The light scattered from each of the points may include a beam travelling initially in the Z axis along the opposite direction of the optical path traveled by the light beam 1018. Each returned light beam in an array of returning light beams 1040 may correspond to one of the incident light beams in array of light beams 1006. Given the asymmetrical properties of unidirectional mirror or beam splitter 1010, the returned light is reflected in the direction of detection optics 1050 in the body.

The detection optics 1050 may include a polarizer 1052 that has a plane of preferred polarization oriented normal to the plane polarization of polarizer 1003. Alternatively, polarizer 1003 and polarizer 1052 may be omitted in some embodiments. The array of returning light 1040 (e.g., array of returning light beams) may pass through imaging optics 1054 in one embodiment. The imaging optics 1054 may include one or more lenses. Alternatively, the detection optics 1050 may not include imaging optics 1054. In one embodiment, the returning light 1040 further passes through a matrix 1056, which may be an array of pinholes. Alternatively, no matrix 1056 is used in some embodiments. The returning light 1040 is then directed onto a detector 1058 in the body.

The detector 1058 is an image sensor having a matrix of sensing elements each representing a pixel of the image. If matrix 1056 is used, then each pixel further corresponds to one pinhole of matrix 1056. In one embodiment, the detector is a charge coupled device (CCD) sensor. In one embodiment, the detector is a complementary metal-oxide semiconductor (CMOS) type image sensor. Other types of image sensors may also be used for detector 1058. In one embodiment, the detector 1058 detects light intensity at each pixel.

In one embodiment, detector 1058 provides data to a computing device, such as computing device 105 of FIG. 1. Thus, each light intensity measured in each of the sensing elements of the detector 1058, is then captured and analyzed.

Intraoral scanner 1000 further includes a control module 1070 in the body connected both to semiconductor laser 1308 and a motor 1072, voice coil or other translation mechanism. In one embodiment, control module 1070 is or includes a field programmable gate array (FPGA) configured to perform control operations. Motor 1072 is linked to focusing optics 1012 for changing a focusing setting of confocal focusing optics 1012. This may adjust the relative location of an imaginary flat or non-flat focal surface of focusing optics 1042 along the Z-axis (e.g., in the imaging axis). Control module 1070 may induce motor 1072 to axially displace (change a location of) one or more lenses of the focusing optics 1012 to change the focal depth of the imaginary flat or non-flat focal surface. In one embodiment, motor 1072 or intraoral scanner 1000 includes an encoder (not shown) that accurately measures a position of one or more lenses of the focusing optics 1012. The encoder may include a sensor paired to a scale that encodes a linear position. The encoder may output a linear position of the one or more lenses of the focusing optics 1012. The encoder may be an optical encoder, a magnetic encoder, an inductive encoder, a capacitive encoder, an eddy current encoder, and so on. After receipt of feedback that the location of the one or more lenses has changed, control module 1070 may induce laser 1308 to generate a light pulse.

Processing logic of the computing device may determine the relative intensity in each pixel of a received intraoral scan over the entire range of focal settings of focusing optics 1012 from received intraoral scan data. Once a certain light point associated with a particular pixel is in focus, the measured intensity will be maximal for that pixel. Thus, by determining the $Z_i$ corresponding to the maximal light intensity or by determining the maximum displacement derivative of the light intensity, for each pixel, the relative position of each light point or spot along the Z axis can be determined for each pixel. Thus, data representative of the three-dimensional pattern of a surface in the teeth segment 1020 or other intraoral object can be obtained.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. An intraoral scanner, comprising:
a body;
a probe at one end of the body, the probe comprising a scanner head;
at least one of one or more light projectors, one or more cameras, an inertial measurement unit (IMU), a programmable logic, or one or more temperature control devices;
a wireless communication module disposed within the body;
one or more optical sensors to receive light that enters the scanner head and generate intraoral scan data based on the light, wherein the wireless communication module is to wirelessly send the intraoral scan data to a computing device;
a replaceable battery disposed within the body;
a backup power source disposed within the body; and a controller disposed within the body, wherein the controller is to:
detect removal of the replaceable battery from the body;
transition the intraoral scanner into a low power mode, wherein to transition the intraoral scanner into the low power mode the controller deactivates at least one of the one or more light projectors, the one or more cameras, the IMU, the programmable logic, or the one or more temperature control devices;
detect insertion of a second replaceable battery into the body; and
transition the intraoral scanner out of the low power mode, wherein to transition the intraoral scanner out of the low power mode the controller reactivates at least one of the one or more light projectors, the one or more cameras, the IMU, the programmable logic, or the one or more temperature control devices.

2. An intraoral scanner, comprising:
a body;
a probe at one end of the body, the probe comprising a scanner head;
a wireless communication module disposed within the body;
one or more optical sensors to receive light that enters the scanner head and generate intraoral scan data based on the light, wherein the wireless communication module is to wirelessly send the intraoral scan data to a computing device;
a replaceable battery disposed within the body;
a backup power source disposed within the body, wherein the backup power source provides up to about 1 Watt of power for up to about 60 seconds; and
a controller disposed within the body, wherein the controller is to:
detect removal of the replaceable battery from the body;
transition the intraoral scanner into a low power mode, wherein the intraoral scanner consumes up to about 1 Watt of power while in the low power mode;
detect insertion of a second replaceable battery into the body; and
transition the intraoral scanner out of the low power mode.

3. The intraoral scanner of claim 1, wherein the backup power source comprises one or more capacitors.

4. The intraoral scanner of claim 1, wherein the controller is further to:
determine when the replaceable battery reaches a threshold charge level; and
output an indicator that the replaceable battery should be replaced responsive to detecting that the replaceable battery has reached the threshold charge level.

5. The intraoral scanner of claim 1, wherein the controller is further to:
initiate a timer responsive to removal of the replaceable battery from the body, wherein the timer indicates an amount of time remaining before the backup power source is exhausted; and
output an indication based on a state of the timer.

6. The intraoral scanner of claim 5, wherein the indication changes as the amount of time remaining before the backup power source is exhausted changes.

7. The intraoral scanner of claim 1, wherein the controller is further to:
determine a remaining charge in the backup power source; and
output an indication based on the remaining charge.

8. An intraoral scanner, comprising:

a body;

a probe at one end of the body, the probe comprising a scanner head;

a wireless communication module disposed within the body;

one or more optical sensors to receive light that enters the scanner head and generate intraoral scan data based on the light, wherein the wireless communication module is to wirelessly send the intraoral scan data to a computing device;

a replaceable battery disposed within the body;

a backup power source disposed within the body; and a controller disposed within the body, wherein the controller is to:

detect removal of the replaceable battery from the body;

transition the intraoral scanner into a low power mode;

determine that the backup power source reaches a threshold power level while no replaceable battery is inserted into the body; and transition the intraoral scanner from the low power mode into a hibernation mode responsive to determining that the backup power source has reached the threshold power level, wherein a first set of components of the intraoral scanner are deactivated during the low power mode, and wherein a second set of components of the intraoral scanner are deactivated during the hibernation mode, wherein the first set of components is a subset of the second set of components.

9. An intraoral scanner, comprising:

a body;

a probe at one end of the body, the probe comprising a scanner head;

a wireless communication module disposed within the body;

one or more optical sensors to receive light that enters the scanner head and generate intraoral scan data based on the light, wherein the wireless communication module is to wirelessly send the intraoral scan data to a computing device;

a replaceable battery disposed within the body;

a backup power source disposed within the body; and a controller disposed within the body, wherein the controller is to:

detect removal of the replaceable battery from the body;

transition the intraoral scanner into a low power mode;

determine that the replaceable battery reaches a threshold power level;

determine that the intraoral scanner is not in use; and transition the intraoral scanner into a hibernation mode responsive to determining that the replaceable battery has reached the threshold power level and that the intraoral scanner is not in use, wherein a first set of components of the intraoral scanner are deactivated during the low power mode, and wherein a second set of components of the intraoral scanner are deactivated during the hibernation mode, wherein the first set of components is a subset of the second set of components.

10. An intraoral scanning system comprising:

an intraoral scanner, comprising:

a body;

a probe at one end of the body, the probe comprising a scanner head;

at least one of one or more light projectors, one or more cameras, an inertial measurement unit (IMU), or one or more temperature control devices;

a wireless communication module disposed within the body;

one or more optical sensors to receive light that enters the scanner head and generate intraoral scan data based on the light, wherein the wireless communication module is to wirelessly send the intraoral scan data to a computing device;

a replaceable battery disposed within the body;

a backup power source disposed within the body; and a controller disposed within the body;

the computing device, to wirelessly receive the intraoral scan data; and a second replaceable battery;

wherein the controller of the intraoral scanner is to:

detect removal of the replaceable battery from the body;

transition the intraoral scanner into a low power mode, wherein to transition the intraoral scanner into the low power mode the controller deactivates at least one of the one or more light projectors, the one or more cameras, the IMU, or the one or more temperature control devices;

detect insertion of the second replaceable battery into the body; and transition the intraoral scanner out of the low power mode, wherein to transition the intraoral scanner out of the low power mode the controller reactivates at least one of the one or more light projectors, the one or more cameras, the IMU, or the one or more temperature control devices.

11. The intraoral scanning system of claim 10, further comprising:

a battery charger to charge the replaceable battery.

12. The intraoral scanning system of claim 11, further comprising:

a cart comprising the computing device, a display, and the battery charger.

13. The intraoral scanning system of claim 10, wherein:

the controller is further to transmit, to the computing device, an indicator that the replaceable battery should be replaced responsive to detecting that the replaceable battery has reached a threshold charge level; and the computing device is to output a prompt to replace the replaceable battery to a display.

14. The intraoral scanning system of claim 10, wherein:

the controller is further to transmit, to the computing device, an indicator that the intraoral scanner is in the low power mode responsive to the intraoral scanner transitioning to the low power mode; and the computing device is to output a prompt that the intraoral scanner is in the low power mode responsive to receiving the indicator.

15. The intraoral scanning system of claim 10, wherein the backup power source provides up to about 1 Watt of power for up to about 60 seconds, and wherein the intraoral scanner consumes up to about 1 Watt of power while in the low power mode.

16. The intraoral scanning system of claim 10, wherein the backup power source comprises one or more capacitors.

17. The intraoral scanning system of claim 10, wherein the controller of the intraoral scanner is further to:

determine when the replaceable battery reaches a threshold charge level; and output an indicator that the replaceable battery should be replaced responsive to detecting that the replaceable battery has reached the threshold charge level.

18. The intraoral scanning system of claim 10, wherein:
the intraoral scanner is to send a notice to the computing device responsive to initiation of the low power mode; and
the computing device is to:
initiate a timer responsive to receipt of the notice, wherein the timer indicates an amount of time remaining before the backup power source is exhausted; and
output, to a display, an indication based on a state of the timer.

19. The intraoral scanning system of claim 10, wherein:
the intraoral scanner is to determine a remaining charge in the backup power source and send a notice of the remaining charge to the computing device; and
the computing device is to output an indication to a display based on the remaining charge.

20. The intraoral scanning system of claim 10, wherein the controller of the intraoral scanner is further to:
determine that the backup power source reaches a threshold power level while no replaceable battery is inserted into the body; and
transition the intraoral scanner from the low power mode into a hibernation mode responsive to determining that the backup power source has reached the threshold power level, wherein a first set of components of the intraoral scanner are deactivated during the low power mode, and wherein a second set of components of the intraoral scanner are deactivated during the hibernation mode, wherein the first set of components is a subset of the second set of components.

21. The intraoral scanning system of claim 10, wherein the controller of the intraoral scanner is further to:
determine that the replaceable battery reaches a threshold power level;
determine that the intraoral scanner is not in use; and
transition the intraoral scanner into a hibernation mode responsive to determining that the replaceable battery has reached the threshold power level and that the intraoral scanner is not in use, wherein a first set of components of the intraoral scanner are deactivated during the low power mode, and wherein a second set of components of the intraoral scanner are deactivated during the hibernation mode, wherein the first set of components is a subset of the second set of components.

22. The intraoral scanning system of claim 21, wherein:
prior to transitioning into the hibernation mode, the intraoral scanner is to send a notice of the hibernation mode to the computing device; and
the computing device is to output an indication that the intraoral scanner is in the hibernation mode to a display.

* * * * *